(12) United States Patent
Hsieh et al.

(10) Patent No.: US 6,933,316 B2
(45) Date of Patent: Aug. 23, 2005

(54) INDOLE COMPOUNDS

(75) Inventors: Hsing-Pang Hsieh, Taipei (TW);
Jing-Ping Liou, Taipei (TW);
Jang-Yang Chang, Taipei (TW);
Chun-Wei Chang, Taipei (TW)

(73) Assignee: National Health Research Institutes, Miaoli (TW)

( * ) Notice: Subject to any disclaimer, the term of this patent is extended or adjusted under 35 U.S.C. 154(b) by 147 days.

(21) Appl. No.: 10/318,337

(22) Filed: Dec. 12, 2002

(65) Prior Publication Data

US 2003/0195244 A1 Oct. 16, 2003

Related U.S. Application Data

(60) Provisional application No. 60/340,317, filed on Dec. 13, 2001.

(51) Int. Cl.[7] ..................... A61K 31/404; C07D 209/04
(52) U.S. Cl. ..................... 514/419; 548/469; 548/490; 548/491
(58) Field of Search ............................ 548/491; 514/419

(56) References Cited

U.S. PATENT DOCUMENTS

| | | | |
|---|---|---|---|
| 3,557,142 A | | 1/1971 | Bell |
| 5,013,837 A | * | 5/1991 | Ward et al. ............. 544/143 |
| 5,468,898 A | * | 11/1995 | Huang et al. ............ 560/41 |
| 5,486,525 A | * | 1/1996 | Summers et al. .......... 514/303 |
| 5,753,664 A | * | 5/1998 | Aono et al. ............. 514/259.4 |
| 5,760,040 A | * | 6/1998 | Yoshida et al. .......... 514/254.09 |
| 6,013,648 A | | 1/2000 | Rinaldi et al. |
| 6,515,141 B1 | * | 2/2003 | Goto et al. ............. 548/492 |

FOREIGN PATENT DOCUMENTS

| | | |
|---|---|---|
| DE | 199 47 863 A1 | 4/2001 |
| WO | WO 92/06088 | 4/1992 |
| WO | WO 98/08818 | 3/1998 |
| WO | WO 00/48606 A1 | 8/2000 |
| WO | WO 00/51983 | 9/2000 |
| WO | WO 01/09103 A2 | 2/2001 |
| WO | WO 01/19794 A2 | 3/2001 |
| WO | WO 01/28557 A1 | 4/2001 |
| WO | WO 01/68654 A2 | 9/2001 |
| WO | WO 02/36561 A1 | 5/2002 |
| WO | WO 02/50007 A2 | 6/2002 |
| WO | WO 02/060872 A1 | 8/2002 |

OTHER PUBLICATIONS

Goto et al (2000): STN International CAPLUS database, Columbus, Ohio, Accession No.: 2001:167965.*
Powell et al. Tetrahedron Letters, 22(47):4751–4754, 1981. XP009023031.

* cited by examiner

*Primary Examiner*—Golam M M Shameem
(74) *Attorney, Agent, or Firm*—Fish & Richardson P.C.

(57) ABSTRACT

Indole compounds of the formula:

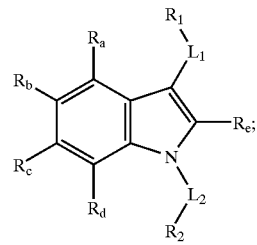

wherein $L_1$ is CO; $L_2$ is a bond; $R_1$ is aryl or heteroaryl; $R_2$ is H, aryl, heteroaryl, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R'', NRC(O)OR', NRC(N)NR'R'', C(O)OR, or C(O)NRR'; each of $R_a$, $R_b$, $R_c$, and $R_d$, independently, is R, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R'', NRC(O)OR', NRC(N)NR'R'', C(O)R, C(O)OR, C(O)NRR', or $R_b$ and $R_c$, $R_a$ and $R_b$, or $R_c$ and $R_d$ taken together are $O(CH_2)_nO$; and $R_e$ is H, alkyl, alkenyl, alkynyl, cyclyl, heterocyclyl, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R'', NRC(O)OR', NRC(N)NR'R'', C(O)R, C(O)OR, or C(O)NRR'; in which each of R, R', and R'', independently, is H, alkyl, alkenyl, alkynyl, aryl, heteroaryl, cyclyl, or heterocyclyl; and n is 1, 2, 3, 4, or 5.

39 Claims, No Drawings

INDOLE COMPOUNDS

RELATED APPLICATION

This application claims priority to U.S. provisional application No. 60/340,317, filed on Dec. 13, 2001, the contents of which are incorporated herein by reference.

BACKGROUND

Cancer treatment can be approached by several modes of therapy, including surgery, radiation, chemotherapy, or a combination of any of these treatments. Among them, chemotherapy is indispensable for inoperable or metastatic forms of cancer.

The microtubule system of eukaryotic cells is an important target for developing anti-cancer agents. More specifically, tubulin polymerization/depolymerization is a popular target for new chemotherapeutic agents. A variety of clinically used compounds (e.g., paclitaxel, epothilone A, vinblastine, combretastatin A-4, dolastatin 10, and colchicine) target tubulin polymerization/depolymerization and disrupt cellular microtubule structures, resulting in mitotic arrest and inhibition of the growth of new vascular epithelial cells. See, e.g., Jordan et al. (1998) *Med. Res. Rev.* 18: 259–296. Thus, those compounds may have the ability to inhibit excessive angiogenesis, which occurs in diseases such as cancer (both solid and hematologic tumors), cardiovascular diseases (e.g., atherosclerosis), chronic inflammation (e.g., rheutatoid arthritis or Crohn's disease), diabetes (e.g., diabetic retinopathy), macular degeneration, psoriasis, endometriosis, and ocular disorders (e.g., corneal or retinal neovascularization). See, e.g., Griggs et al. (2002) *Am. J. Pathol.* 160(3): 1097–103.

Take combretastatin A-4 (CA-4) for example. CA-4, isolated by Pettit and co-workers in 1982 (*Can. J. Chem.* 60: 1374–1376), is one of the most potent anti-mitotic agents derived from the stem wood of the South African tree *Combretum caffrum*. This agent shows strong cytotoxicity against a wide variety of human cancer cells, including multi-drug resistant cancer cells. See, e.g., Pettit et al. (1995) *J. Med. Chem.* 38: 1666–1672; Lin et al. (1989) *Biochemistry* 28: 6984–6991; and Lin et al. (1988) *Mol. Pharmacol.* 34: 200–208. CA-4, structurally similar to colchicines, possesses a higher affinity for the colchicine binding site on tubulin than colchicine itself. Pettit et al. (1989) *Experientia* 45: 209–211. It also has been shown to possess anti-angiogenesis activity. See Pinney et al. WO 01/68654A2. The low water-solubility of CA-4 limits its efficacy in vivo. See, e.g., Chaplin et al. (1999) *Anticancer Research* 19: 189–195; and Grosios et al. (1999) *Br. J. Cancer* 81: 1318–1327.

Identification of compounds that also target the microtubule system (e.g., tubulin polymerization/depolymerization) can lead to new therapeutics useful in treating or preventing cancer or symptoms associated with cancer.

SUMMARY

This invention is based on the discovery that indole compounds have anti-cancer activities, and function via targeting the microtubule system (e.g., tubulin polymerization/depolymerization) or others.

In one aspect, this invention features indole compounds of the following formula:

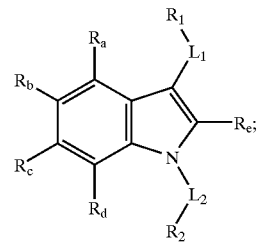

wherein $L_1$ is C(O); $L_2$ is a bond; $R_1$ is aryl or heteroaryl; $R_2$ is H, aryl, heteroaryl, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R'', NRC(O)OR', NRC(N)NR'R'', C(O)OR, or C(O)NRR'; each of $R_a$, $R_b$, $R_c$, and $R_d$, independently, is R, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R'', NRC(O)OR', NRC(N)NR'R'', C(O)R, C(O)OR, C(O)NRR', or $R_b$ and $R_c$, $R_a$ and $R_b$, or $R_c$ and $R_d$ taken together are $O(CH_2)_nO$; and $R_e$ is H, alkyl, alkenyl, alkynyl, cyclyl, heterocyclyl, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R'', NRC(O)OR', NRC(N)NR'R'', C(O)R, C(O)OR, or C(O)NRR'; in which each of R, R', and R'', independently, is H, alkyl, alkenyl, alkynyl, aryl, heteroaryl, cyclyl, or heterocyclyl; and n is 1, 2, 3, 4, or 5. Note that the left atom shown in any substituted group described above is closest to the indole ring. Also note that when $R_a$, $R_b$, $R_c$, and $R_d$ are R, the just-described indole compounds may have different R moieties. The same rule applies to other similar situations.

Referring to the just-described indole compounds, a subset of these compounds is featured by that $R_e$ is H or alkyl. In these compounds, each of $R_a$, $R_b$, $R_c$, and $R_d$, independently, can be H, alkyloxy, alkyl, or halogen (e.g., $R_c$ is alkyloxy, alkyl, or halogen, and each of $R_a$, $R_b$, and $R_d$ is H). $R_1$ can be 3,4,5-trimethoxyphenyl. In some embodiments, one, two, or three of $R_a$, $R_b$, $R_c$, and $R_d$ are alkyloxy, alkyl, or halogen. Preferably, one of $R_a$, $R_b$, $R_c$, and $R_d$ is alkyloxy, alkyl, or halogen, and the others are H. More preferably, $R_c$ is alkyloxy, alkyl, or halogen (e.g., $R_c$ is $OCH_3$, $OCH_2CH_3$, $CH_3$, F, or Br), and each of $R_a$, $R_b$, and $R_d$ is H. $R_2$ can be H, OR, C(O)NRR', C(O)OR (e.g., $C(O)OC(CH_3)_3$, or $C(O)OC_6H_5$), or $SO_2R$ (e.g., $SO_2CH_3$, or $SO_2(4-CO_2H-C_6H_4)$). In other embodiments, $R_b$ and $R_c$ taken together are $O(CH_2)_nO$, and each of $R_a$ and $R_d$ is H, in which n is 1 or 2. Another subset of the indole compounds are those compounds wherein $R_1$ is 5, 6, or 7-member aryl or heteroaryl tri-substituted with alkyloxy (e.g., 3,4,5-trimethoxyphenyl).

In another aspect, this invention features indole compounds of the formula above, wherein $L_1$ is C(O); $L_2$ is a bond; $R_1$ is aryl or heteroaryl; $R_2$ is alkyl, alkenyl, alkynyl, cyclyl, or heterocyclyl; each of $R_a$, $R_b$, $R_c$, and $R_d$, independently, is R, halogen, nitro, isothionitro, OR, OC(O)R, OC(O)OR, OC(O)NRR', $SO_2R$, $SO_3R$, $SO_2NRR'$, SR, $NRSO_2NR'R''$, $NRSO_2R'$, $NRSO_3R'$, NRC(O)R', NRC(O)NR'R'', NRC(O)OR', NRC(N)NR'R'', C(O)R, C(O)OR, C(O)NRR', or $R_b$ and $R_c$, $R_a$ and $R_b$, or $R_c$ and $R_d$ taken together are $O(CH_2)_nO$; and $R_e$ is H, alkyl, alkenyl, alkynyl, aryl, heteroaryl, cyclyl, heterocyclyl, halogen, nitro, nitroso, cyano, azide, isothionitro, OR, OC(O)R, OC(O)OR, OC(O)

NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R", NRC(O)OR', NRC(N)NR'R", C(O)R, C(O)OR, or C(O)NRR'; in which each of R, R', and R", independently, is H, alkyl, alkenyl, alkynyl, aryl, heteroaryl, cyclyl, or heterocyclyl; and n is 1, 2, 3, 4, or 5.

Referring to the just-described indole compounds, a subset of these compounds is featured by that $R_e$ is H or alkyl. In these compounds, each of $R_a$, $R_b$, $R_c$, and $R_d$, independently, can be H, alkyloxy, alkyl, or halogen (e.g., $R_c$ is alkyloxy, alkyl, or halogen, and each of $R_a$, $R_b$, and $R_d$ is H). $R_1$ can be 3,4,5-trimethoxylphenyl. In some embodiments, one, two, or three of $R_a$, $R_b$, $R_c$, and $R_d$ are alkyloxy, alkyl, or halogen. Preferably, one of $R_a$, $R_b$, $R_c$, and $R_d$ is alkyloxy, alkyl, or halogen, and the others are H. More preferably, $R_c$ is alkyloxy, alkyl, or halogen (e.g., $R_c$ is $OCH_3$), and each of $R_a$, $R_b$, and $R_d$ is H. $R_2$ can be alkyl, alkenyl, or alkynyl (e.g., $CH_3$, $C_2H_5$, $CH_2CH=CH_2$, $CH_2C\equiv CH$, or $CH_2$-4-pyridinyl). In other embodiments, $R_b$ and $R_c$ taken together are $O(CH_2)_nO$, and each of $R_a$ and $R_d$ is H, in which n is 1 or 2. Another subset of the indole compounds are those compounds wherein $R_1$ is 5, 6, or 7-member aryl or heteroaryl tri-substituted with alkyloxy (e.g., 3,4,5-trimethoxylphenyl).

In still another aspect, this invention features indole compounds of the formula above, wherein $L_1$ is C(O); $L_2$ is a bond; $R_1$ is aryl or heteroaryl; $R_2$ is COR'''; each of $R_a$, $R_b$, $R_c$, and $R_d$, independently, is R, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R", NRC(O)OR', NRC(N)NR'R", C(O)R, C(O)OR, C(O)NRR', or $R_b$ and $R_c$, $R_a$ and $R_b$, or $R_c$ and $R_d$ taken together are $O(CH_2)_nO$; and $R_e$ is R, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R", NRC(O)OR', NRC(N)NR'R", C(O)R, C(O)OR, or C(O)NRR'; in which each of R, R', and R" independently, is H, alkyl, alkenyl, alkynyl, aryl, heteroaryl, cyclyl, or heterocyclyl; R''' is H, alkyl, alkenyl, alkynyl, heteroaryl, cyclyl, or heterocyclyl; and n is 1, 2, 3, 4, or 5.

Referring to the just-described indole compounds, a subset of these compounds is featured by that $R_e$ is H or alkyl. In these compounds, each of $R_a$, $R_b$, $R_c$, and $R_d$, independently, can be H, alkyloxy, alkyl, or halogen (e.g., $R_c$ is alkyloxy, alkyl, or halogen, and each of $R_a$, $R_b$, and $R_d$ is H). $R_1$ can be 3,4,5-trimethoxylphenyl. In some embodiments, one, two, or three of $R_a$, $R_b$, $R_c$, and $R_d$ are alkyloxy, alkyl, or halogen. Preferably, one of $R_a$, $R_b$, $R_c$, and $R_d$ is alkyloxy, alkyl, or halogen, and the others are H. More preferably, $R_c$ is alkyloxy, alkyl, or halogen (e.g., $R_c$ is $OCH_3$), and each of $R_a$, $R_b$, and $R_d$ is H. R''' is alkyl (e.g., $CH_2NRR'$), alkenyl (e.g., (E)-CH=CH—$C_6H_5$), or heteroaryl (e.g., 2-pyridinyl, 3-pyridinyl, 2-furyl, or 2-thienyl). In other embodiments, $R_b$ and $R_c$ taken together are $O(CH_2)_nO$, and each of $R_a$ and $R_d$ is H, in which n is 1 or 2. Another subset of the indole compounds are those compounds wherein $R_1$ is 5, 6, or 7-member aryl or heteroaryl tri-substituted with alkyloxy (e.g., 3,4,5-trimethoxylphenyl).

In a further aspect, this invention features indole compounds of the formula above, $L_1$ is a bond; $L_2$ is C(O); $R_1$ is H, alkenyl, alkynyl, aryl, heteroaryl, cyclyl, heterocyclyl, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R", NRC(O)OR', NRC(N)NR'R", C(O)R, C(O)OR, or C(O)NRR'; $R_2$ is aryl or heteroaryl; each of $R_a$, $R_b$, $R_c$, and $R_d$, independently, is H, unsubstituted alkyl, alkenyl, alkynyl, aryl, heteroaryl, cyclyl, heterocyclyl, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R", NRC(O)OR', NRC(N)NR'R", C(O)R, C(O)OR, C(O)NRR', or $R_b$ and $R_c$, $R_a$ and $R_b$, or $R_c$ and $R_d$ taken together are $O(CH_2)_nO$; and $R_e$ is H, alkyl, alkenyl, alkynyl, cyclyl, heterocyclyl, heteroaryl, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R", NRC(O)OR', NRC(N)NR'R", C(O)R, C(O)OR, or C(O)NRR'; in which each of R, R', and R" independently, is H, alkyl, alkenyl, alkynyl, aryl, heteroaryl, cyclyl, or heterocyclyl; and n is 1, 2, 3, 4, or 5.

Referring to the just-described indole compounds, a subset of these compounds is featured by that $R_e$ is H or alkyl. In these compounds, each of $R_a$, $R_b$, $R_c$, and $R_d$, independently, can be H, alkyloxy, alkyl, or halogen (e.g., $R_b$ is alkyloxy, alkyl, or halogen, and each of $R_a$, $R_c$, and $R_d$ is H). $R_2$ can be 3,4,5-trimethoxylphenyl or 3,5-dimethoxyphenyl. In some embodiments, one, two, or three of $R_a$, $R_b$, $R_c$, and $R_d$ are alkyloxy, alkyl, or halogen. Preferably, one of $R_a$, $R_b$, $R_c$, and $R_d$ is alkyloxy, alkyl, or halogen, and the others are H. More preferably, $R_b$ is alkyloxy, alkyl, or halogen (e.g., $R_b$ is $OCH_3$), and each of $R_a$, $R_c$, and $R_d$ is H. $R_1$ can be H or alkyl. In other embodiments, $R_b$ and $R_c$ taken together are $O(CH_2)_nO$, and each of $R_a$ and $R_d$ is H, in which n is 1 or 2. Another subset of the indole compounds are those compounds wherein $R_2$ is 5, 6, or 7-member aryl or heteroaryl tri-substituted with alkyloxy (e.g., 3,4,5-trimethoxylphenyl).

In another aspect, this invention features indole compounds of the formula above, wherein $L_1$ is O, S, NR, $SO_2$, or $CH_2$; $L_2$ is a bond; $R_1$ is 5, 6, or 7-member aryl or heteroaryl tri-substituted with alkyloxy; and each of $R_2$, $R_a$, $R_b$, $R_c$, $R_d$, and $R_e$, independently, R, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R", NRC(O)OR', NRC(N)NR'R", C(O)R, C(O)OR, C(O)NRR', or $R_b$ and $R_c$, $R_a$ and $R_b$, or $R_c$ and $R_d$ taken together are $O(CH_2)_nO$; in which each of R, R', and R", independently, is H, alkyl, alkenyl, alkynyl, aryl, heteroaryl, cyclyl, or heterocyclyl; and n is 1, 2, 3, 4, or 5.

Referring to the just-described indole compounds, a subset of these compounds is featured by $R_e$ is H or alkyl. In these compounds, each of $R_a$, $R_b$, $R_c$, and $R_d$, independently, can be H, alkyloxy, alkyl, or halogen (e.g., $R_c$ is alkyloxy, alkyl, or halogen, and each of $R_a$, $R_b$, and $R_d$ is H). $R_1$ can be 3,4,5-trimethoxylphenyl. In some embodiments, one, two, or three of $R_a$, $R_b$, $R_c$, and $R_d$ are alkyloxy, alkyl, or halogen. Preferably, one of $R_a$, $R_b$, $R_c$, and $R_d$ is alkyloxy, alkyl, or halogen, and the others are H. More preferably, $R_c$ is alkyloxy, alkyl, or halogen (e.g., $R_c$ is $OCH_3$ or $CH_3$), and each of $R_a$, $R_b$, and $R_d$ is H. In other embodiments, $R_b$ and $R_c$ taken together are $O(CH_2)_nO$, and each of $R_a$ and $R_d$ is H, in which n is 1 or 2. Another subset of the indole compounds are those compounds wherein $R_1$ is 5, 6, or 7-member aryl or heteroaryl tri-substituted with alkyloxy (e.g., 3,4,5-trimethoxylphenyl).

Further, in still another aspect, this invention features indole compounds of the formula above, wherein $L_1$ is a bond; $L_2$ is O, S, NR, $SO_2$, or $CH_2$; $R_2$ is 5, 6, or 7-member aryl or heteroaryl tri-substituted with alkyloxy; and each of $R_1$, $R_a$, $R_b$, $R_c$, $R_d$, and $R_e$, independently, R, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R'', NRC(O)OR', NRC(N)NR'R'', C(O)R, C(O)OR, C(O)NRR', or $R_b$ and $R_c$, $R_a$ and $R_b$, or $R_c$ and $R_d$ taken together are $O(CH_2)_nO$; in which each of R, R', and R'', independently, is H, alkyl, alkenyl, alkynyl, aryl, heteroaryl, cyclyl, or heterocyclyl; and n is 1, 2, 3, 4, or 5.

Referring to the just-described indole compounds, a subset of these compounds is featured by $R_e$ is H or alkyl. In these compounds, each of $R_a$, $R_b$, $R_c$, and $R_d$, independently, can be H, alkyloxy, alkyl, or halogen (e.g., $R_b$ is alkyloxy, alkyl, or halogen, and each of $R_a$, $R_c$, and $R_d$ is H). $R_2$ can be 3,4,5-trimethoxylphenyl. In some embodiments, one, two, or three of $R_a$, $R_b$, $R_c$, and $R_d$ are alkyloxy, alkyl, or halogen. Preferably, one of $R_a$, $R_b$, $R_c$, and $R_d$ is alkyloxy, alkyl, or halogen, and the others are H. More preferably, $R_b$ is alkyloxy, alkyl, or halogen (e.g., $R_b$ is $OCH_3$ or $CH_3$), and each of $R_a$, $R_c$, and $R_d$ is H. In other embodiments, $R_b$ and $R_c$ taken together are $O(CH_2)_nO$, and each of $R_a$ and $R_d$ is H, in which n is 1 or 2. Another subset of the indole compounds are those compounds wherein $R_2$ is 5, 6, or 7-member aryl or heteroaryl tri-substituted with alkyloxy (e.g., 3,4,5-trimethoxylphenyl).

This invention also features indole compounds of the formula above, wherein $L_1$ is O, S, NR, $SO_2$, or $CH_2$; $L_2$ is a bond; $R_1$ is 5, 6, or 7-member aryl or heteroaryl di-substituted with alkyloxy; and each of $R_2$, $R_a$, $R_b$, $R_c$, $R_d$, and $R_e$, independently, R, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R'', NRC(O)OR', NRC(N)NR'R'', C(O)R, C(O)OR, C(O)NRR', or $R_b$ and $R_c$, $R_a$ and $R_b$, or $R_c$ and $R_d$ taken together are $O(CH_2)_nO$; in which each of R, R', and R'', independently, is H, alkyl, alkenyl, alkynyl, aryl, heteroaryl, cyclyl, or heterocyclyl; and n is 1, 2, 3, 4, or 5. In the just-described indole compounds, $R_1$ can be 3,5-dimethoxylphenyl.

Also within the scope of this invention are indole compounds of the formula above, wherein $L_1$ is a bond; $L_2$ is O, S, NR, $SO_2$, or $CH_2$; $R_2$ is 5, 6, or 7-member aryl or heteroaryl di-substituted with alkyloxy; and each of $R_1$, $R_a$, $R_b$, $R_c$, $R_d$, and $R_e$, independently, R, halogen, nitro, nitroso, cyano, azide, isothionitro, OR, OC(O)R, OC(O)OR, OC(O) NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R'', NRC(O)OR', NRC(N)NR'R'', C(O)R, C(O)OR, C(O)NRR', or $R_b$ and $R_c$, $R_a$ and $R_b$, or $R_c$ and $R_d$ taken together are $O(CH_2)_nO$ in which each of R, R', and R'', independently, is H, alkyl, alkenyl, alkynyl, aryl, heteroaryl, cyclyl, or heterocyclyl; and n is 1, 2, 3, 4, or 5. In the just-described indole compounds, $R_2$ can be 3,5-dimethoxylphenyl.

Unless specifically pointed out, alkyl, alkenyl, alkynyl, aryl, heteroaryl, cyclyl, and heterocyclyl mentioned herein include both substituted and unsubstituted moieties. The term "substituted" refers to one or more substituents (which may be the same or different), each replacing a hydrogen atom. Examples of substituents include, but are not limited to, halogen, cyano, nitro, hydroxyl, amino, mercapto, alkyl, alkenyl, alkynyl, aryl, heteroaryl, cyclyl, heterocyclyl, alkyloxy, aryloxy, alksulfanyl, arylsulfanyl, alkylamino, arylamino, dialkylamino, diarylamino, alkylcarbonyl, arylcarbonyl, heteroarylcarbonyl, alkylcarboxyl, arylcarboxyl, heteroarylcarboxyl, alkyloxycarbonyl, aryloxycarbonyl, heteroaryloxycarbonyl, alkylcarbamido, arylcarbamido, heterocarbamido, alkylcarbamyl, arylcarbamyl, heterocarbamyl, wherein each of alkyl (including alk), alkenyl, aryl, heteroaryl, cyclyl, and heterocyclyl is optionally substituted with halogen, cyano, nitro, hydroxyl, amino, mercapto, alkyl, aryl, heteroaryl, alkyloxy, aryloxy, alkylcarbonyl, arylcarbonyl, alkylcarboxyl, arylcarboxyl, alkyloxycarbonyl, or aryloxycarbonyl.

As used herein, the term "alkyl" refers to a straight-chained or branched alkyl group containing 1 to 6 carbon atoms. Examples of alkyl groups include methyl, ethyl, n-propyl, isopropyl, tert-butyl, and n-pentyl. Similarly, the term "alkenyl" or "alkynyl" refers to a straight-chained or branched alkenyl or alkynyl group containing 2 to 6 carbon atoms.

The term "aryl" refers to a hydrocarbon ring system (mono-cyclic or bi-cyclic) having at least one aromatic ring. Examples of aryl moieties include, but are not limited to, phenyl, naphthyl, and pyrenyl.

The term "heteroaryl" refers to a hydrocarbon ring system (mono-cyclic or bi-cyclic) having at least one aromatic ring which contains at least one heteroatom such as O, N, or S as part of the ring system and the reminder being carbon. Examples of heteroaryl moieties include, but are not limited to, furyl, pyrrolyl, thienyl, oxazolyl, imidazolyl, thiazolyl, pyridinyl, pyrimidinyl, quinazolinyl, and indolyl.

The terms "cyclyl" and "heterocyclyl" refer to a partially or fully saturated mono-cyclic or bi-cyclic ring system having from 4 to 14 ring atoms. A heterocyclyl ring contains one or more heteroatoms (e.g., O, N, or S) as part of the ring system and the remainder being carbon. Exemplary cyclyl and heterocyclyl rings are cyclohexane, piperidine, piperazine, morpholine, thiomorpholine, and 1,4-oxazepane.

Set forth below are exemplary compounds of this invention:

(6-Methoxy-1H-indol-3-yl)-(3,4,5-trimethoxy-phenyl)-methanone (Compound 1);

(6-Methyl-1H-indol-3-yl)-(3,4,5-trimethoxy-phenyl)-methanone (Compound 2);

(6-Methoxy-1-pyridin-4-ylmethyl-1H-indol-3-yl)-(3,4,5-trimethoxy-phenyl)-methanone (Compound 3);

(1-Allyl-6-methoxy-1H-indol-3-yl)-(3,4,5-trimethoxy-phenyl)-methanone (Compound 4);

[6-Methoxy-1-(pyridine-2-carbonyl)-1H-indol-3-yl]-(3,4,5-trimethoxy-phenyl)-methanone (Compound 5);

6-Methoxy-3-(3,4,5-trimethoxy-benzoyl)-indole-1-carboxylic acid tert-butyl ester (Compound 6);

(1-Methanesulfonyl-6-methoxy-1H-indol-3-yl)-(3,4,5-trimethoxy-phenyl)-methanone (Compound 7);

[6-Methoxy-1-(morpholine-4-carbonyl)-1H-indol-3-yl]-(3,4,5-trimethoxy-phenyl)-methanone (Compound 8);

[6-Methoxy-1-(2-piperidin-1-yl-ethyl)-1H-indol-3-yl]-(3,4,5-trimethoxy-phenyl)-methanone (Compound 9);

(6-Methoxy-1-prop-2-ynyl-1H-indol-3-yl)-(3,4,5-trimethoxy-phenyl)-methanone (Compound 10);

6-Methoxy-3-(3,4,5-trimethoxy-benzoyl)-indole-1-carboxylic acid dimethylamide (Compound 11);

1-[6-Methoxy-3-(3,4,5-trimethoxy-benzoyl)-indol-1-yl]-3-phenyl-propenone (Compound 12);

6-Methoxy-3-(3,4,5-trimethoxy-benzoyl)-indole-1-carboxylic acid phenyl ester (Compound 13);

[1-(5-Dimethylamino-naphthalene-1-sulfonyl)-6-methoxy-1H-indol-3-yl]-(3,4,5-trimethoxy-phenyl)-methanone (Compound 14);

[1-(2-Dimethylamino-ethyl)-6-methoxy-1H-indol-3-yl]-(3,4,5-trimethoxy-phenyl)-methanone (Compound 15);

(6-Methoxy-1-methyl-1H-indol-3-yl)-(3,4,5-trimethoxy-phenyl)-methanone (Compound 16);

[1-(2-Amino-ethyl)-6-methoxy-1H-indol-3-yl]-(3,4,5-trimethoxy-phenyl)-methanone (Compound 17);

[1-(Furan-2-carbonyl)-6-methoxy-1H-indol-3-yl]-(3,4,5-trimethoxy-phenyl)-methanone (Compound 18);

(1-Ethyl-6-methoxy-1H-indol-3-yl)-(3,4,5-trimethoxy-phenyl)-methanone (Compound 19);

[6-Methoxy-1-(2-morpholin-4-yl-ethyl)-1H-indol-3-yl]-(3,4,5-trimethoxy-phenyl)-methanone (Compound 20);

[1-(4-Chloro-benzyl)-6-methoxy-1H-indol-3-yl]-(3,4,5-trimethoxy-phenyl)-methanone (Compound 21);

(1-Benzyl-6-methoxy-1H-indol-3-yl)-(3,4,5-trimethoxy-phenyl)-methanone (Compound 22);

(6-Fluoro-1H-indol-3-yl)-(3,4,5-trimethoxy-phenyl)-methanone (Compound 23);

(6-Bromo-1H-indol-3-yl)-(3,4,5-trimethoxy-phenyl)-methanone (Compound 24);

(4,5,6-Trimethoxy-1H-indol-3-yl)-(3,4,5-trimethoxy-phenyl)-methanone (Compound 25);

6-Methoxy-3-(3,4,5-trimethoxy-benzyl)-1H-indole (Compound 26);

(5-Methoxy-indol-1-yl)-(3,4,5-trimethoxy-phenyl)-methanone (Compound 27);

(6-Fluoro-indol-1-yl)-(3,4,5-trimethoxy-phenyl)-methanone (Compound 28);

(5,6-Dimethoxy-indol-1-yl)-(3,4,5-trimethoxy-phenyl)-methanone (Compound 29);

(5,6-Bis-benzyloxy-indol-1-yl)-(3,4,5-trimethoxy-phenyl)-methanone (Compound 30);

[1,3]Dioxolo[4,5-f]indol-5-yl-(3,4,5-trimethoxy-phenyl)-methanone (Compound 31);

[3-(2-Dimethylamino-ethyl)-5-methoxy-indol-1-yl]-(3,4,5-trimethoxy-phenyl)-methanone (Compound 32);

N-{2-[5-Methoxy-1-(3,4,5-trimethoxy-benzoyl)-1H-indol-3-yl]-ethyl}-acetamide (Compound 33);

(5,6-Dimethoxy-1H-indol-3-yl)-(3,4,5-trimethoxy-phenyl)-methanone (Compound 34);

(5-Methoxy-2-methyl-indol-1-yl)-(3,4,5-trimethoxy-phenyl)-methanone (Compound 35);

(1,6-Dimethyl-1H-indol-3-yl)-(3,4,5-trimethoxy-phenyl)-methanone (Compound 36);

(1-Ethyl-6-methyl-1H-indol-3-yl)-(3,4,5-trimethoxy-phenyl)-methanone (Compound 37);

(1-Allyl-6-methyl-1H-indol-3-yl)-(3,4,5-trimethoxy-phenyl)-methanone (Compound 38);

(5-Ethyl-5H-[1,3]dioxolo[4,5-f]indol-7-yl)-(3,4,5-trimethoxy-phenyl)-methanone (Compound 39);

(5-Methyl-5H-[1,3]dioxolo[4,5-f]indol-7-yl)-(3,4,5-trimethoxy-phenyl)-methanone (Compound 40);

(5-Allyl-5H-[1,3]dioxolo[4,5-f]indol-7-yl)-(3,4,5-trimethoxy-phenyl)-methanone (Compound 41);

(6-Methoxy-2-methyl-1H-indol-3-yl)-(3,4,5-trimethoxy-phenyl)-methanone (Compound 42);

6-Methoxy-3-(3,4,5-trimethoxy-phenylsulfanyl)-1H-indole (Compound 43);

(6-Ethoxy-1H-indol-3-yl)-(3,4,5-trimethoxy-phenyl)-methanone (Compound 44);

(7-Methoxy-1H-indol-3-yl)-(3,4,5-trimethoxy-phenyl)-methanone (Compound 45);

(4-Methoxy-1H-indol-3-yl)-(3,4,5-trimethoxy-phenyl)-methanone (Compound 46);

(5-Methoxy-4-methyl-1H-indol-3-yl)-(3,4,5-trimethoxy-phenyl)-methanone (Compound 47);

(4,7-Dimethoxy-1H-indol-3-yl)-(3,4,5-trimethoxy-phenyl)-methanone (Compound 48);

(4,6-Dimethoxy-1H-indol-3-yl)-(3,4,5-trimethoxy-phenyl)-methanone (Compound 49);

(5,7-Dimethoxy-1H-indol-3-yl)-(3,4,5-trimethoxy-phenyl)-methanone (Compound 50);

{6-Methoxy-1-[4-(4-nitro-phenyl)-furan-2-ylmethyl]-1H-indol-3-yl}-(3,4,5-trimethoxy-phenyl)-methanone (Compound 51);

(6-Hydroxy-1H-indol-3-yl)-(3,4,5-trimethoxy-phenyl)-methanone (Compound 52);

6-Methoxy-3-(3,4,5-trimethoxy-benzenesulfonyl)-1H-indole (Compound 53);

[1-(2-Dimethylamino-ethyl)-4,5,6-trimethoxy-1H-indol-3-yl]-(3,4,5-trimethoxy-phenyl)-methanone (Compound 54), 4-[6-Methoxy-3-(3,4,5-trimethoxy-benzoyl)-indole-1-sulfonyl]-benzoic acid (Compound 55);

(5H-[1,3]Dioxolo[4,5-f]indol-7-yl)-(3,4,5-trimethoxy-phenyl)-methanone (Compound 56)

{2-[6-Methoxy-3-(3,4,5-trimethoxy-benzoyl)-indol-1-yl]-2-oxo-ethyl}-carbamic acid 9H-fluoren-9-yl-methyl ester (Compound 57);

[6-Methoxy-1-(pyridine-3-carbonyl)-1H-indol-3-yl]-(3,4,5-trimethoxy-phenyl)-methanone (Compound 58);

[6-Methoxy-1-(thiophene-2-carbonyl)-1H-indol-3-yl]-(3,4,5-trimethoxy-phenyl)-methanone (Compound 59);

(5-Methyl-indol-1-yl)-(3,4,5-trimethoxy-phenyl)-methanone (Compound 60; and (3,5-Dimethoxy-phenyl)-(5-methoxy-indol-1-yl)-methanone (Compound 61).

Another aspect of the present invention relates to a pharmaceutical composition that contains a pharmaceutically acceptable carrier and an effective amount of at least one of the indole compounds described above.

A further aspect of this invention relates to a method for treating cancer, e.g., carcinoma or sarcoma. The method includes administering to a subject (e.g., a human or animal) in need thereof an effective amount of an indole compound of the formula above, wherein each of $L_1$ and $L_2$, independently, is a bond, CO, O, S, NR, $SO_2$, or $CH_2$; in which if one of $L_1$ and $L_2$ is a bond, the other one is CO, O, S, NR, $SO_2$, or $CH_2$; each of $R_1$ and $R_2$, independently, is R, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R'', NRC(O)OR', NRC(N)NR'R'', C(O)R, C(O)OR, C(O)NRR'; each of $R_a$, $R_b$, $R_c$, $R_d$ and $R_e$, independently, R, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R'', NRC(O)OR', NRC(N)NR'R'', C(O)R, C(O)OR, C(O)NRR', or $R_b$ and $R_c$, $R_a$ and $R_b$, or $R_c$ and $R_d$ taken together are $O(CH_2)_nO$; and in which each of R, R', and R'', independently, is H, alkyl, alkenyl, alkynyl, aryl, heteroaryl, cyclyl, or heterocyclyl; and n is 1, 2, 3, 4, or 5.

In still another aspect, this invention features a method for inhibiting tubulin polymerization. The method includes administering to a subject (e.g., a human or animal) in need thereof an effective amount of one or more of the just described indole compounds.

In yet another aspect, this invention features a method for treating an angiogenesis-related disorder. The method includes administering to a subject (e.g., a human or animal) in need thereof an effective amount of one or more of the just described indole compounds.

This invention also includes a method for inhibiting cellular proliferation or inducing the killing of hyperproliferation cells. The method involves treatment of a disorder characterized by aberrant cellular proliferation or differentiation in a subject (e.g., a human or animal). The method comprises administering to the subject an effective amount of one or more the just described indole compounds.

The methods described above can also include the step of identifying that the subject is in need of treatment of diseases or disorders described above. The identification can be in the judgment of a subject or a health professional and can be subjective (e.g., opinion) or objective (e.g., measurable by a test or a diagnostic method).

All of the indole compounds described above include the compounds themselves, as well as their salts and their prodrugs, if applicable. The salts, for example, can be formed between a positively charged substituent (e.g., amino) on a compound and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as teteramethylammonium ion. Examples of prodrugs include esters and other pharmaceutically acceptable derivatives, which, upon administration to a subject, are capable of providing the indole compounds described above (see Goodman and Gilman's, The Pharmacological basis of Therapeutics, $8^{th}$ ed., McGraw-Hill, Int. Ed. 1992, "Biotransformation of Drugs").

In addition, some of the just-described indole compounds have one or more double bonds, or one or more asymmetric centers. Such compounds can occur as racemates, racemic mixtures, single enantiomers, individual diastereomers, diastereomeric mixtures, and cis- or trans- or E- or Z-double bond isomeric forms.

Further, the aforementioned indole compounds also include their N-oxides. The term "N-oxides" refers to one or more nitrogen atoms, when present in an indole compound, are in N-oxide form, i.e., N→O.

Combinations of substituents and variables envisioned by this invention are only those that result in the formation of stable indole compounds without departing from the spirit and scope thereof. The term "stable", as used herein, refers to compounds which possess stability sufficient to allow manufacture and which maintains the integrity of the compound for a sufficient period of time to be useful for the purposes detailed herein (e.g., treating cancer).

Also within the scope of this invention are a composition containing one or more of the indole compounds described above for use in treating diseases or disorders described above, and the use of such a composition for the manufacture of a medicament for the aforementioned treatment.

Other features or advantages of the present invention will be apparent from the following detailed description of several embodiments, and also from the appending claims.

DETAILED DESCRIPTION

The indole compounds described above can be prepared by methods well known in the art, as well as by the synthetic routes disclosed herein. For example, as shown in Scheme 1 below, one can couple an indole compound with an acyl chloride. The 6-position of the starting indole compound can be alkyloxy, e.g., $OCH_3$. The 2, 4, 5, and 7-positions of the starting indole may be substituted. The product of the coupling reaction, referred to simply as an "indol-3-yl-arylmethanone" for brevity, can be converted to a 1-substituted-indol-3-yl-aryl-methanone by coupling the indol-3-yl-arylmethanone with a halide, e.g., $R_eCOCl$, $R_eCH_2Cl$, or $R_eSO_2Cl$. Alternatively, the indol-3-yl-aryl-methanone can be reduced to an indol-3-yl-aryl-methane, which can be further reacted with a halide to produce a 1-substituted, indol-3-yl-aryl-methane. Once again, although the 2, 4, 5, and 7-positions of the starting indole compound may be substituted, the compounds are referred to as 1-substituted-indol-3-yl-aryl-methane for brevity.

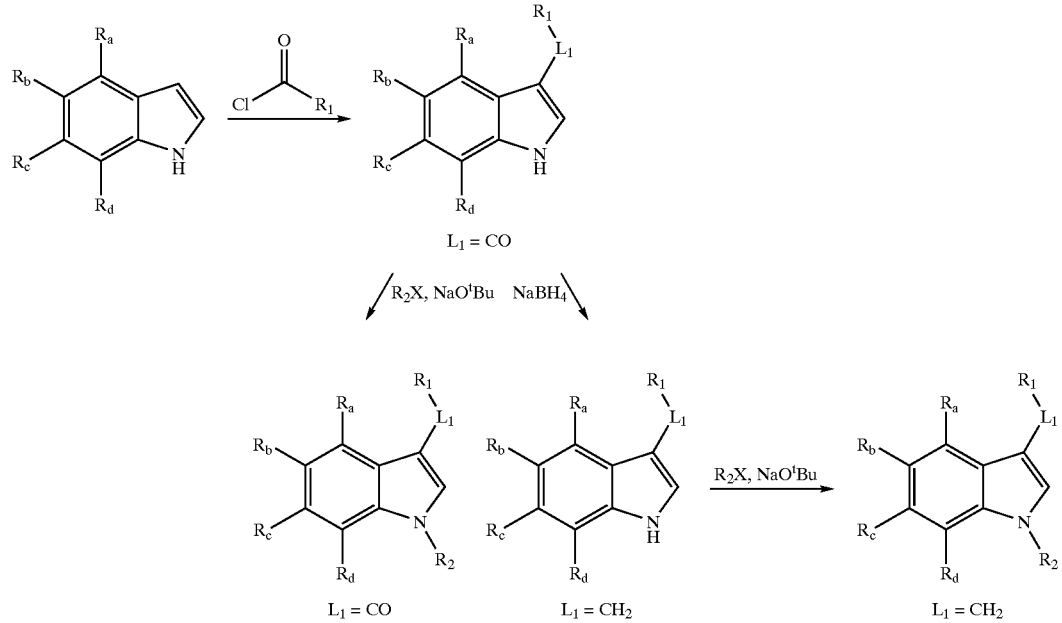

Scheme 1

In another example, as shown in Scheme 2 below, one can couple an indole compound with an acyl chloride in the presence of a base (e.g., NaO$^t$Bu). The 5-position of the starting indole can be alkyloxy, e.g., OCH$_3$. The 2, 4, 6, and 7-positions of the indole may be H, or substituted. The coupling reaction produces an indol-1-yl-aryl-methanone of interest. The product of the coupling reaction can be reduced to an indol-1-yl-aryl-methane.

Scheme 2

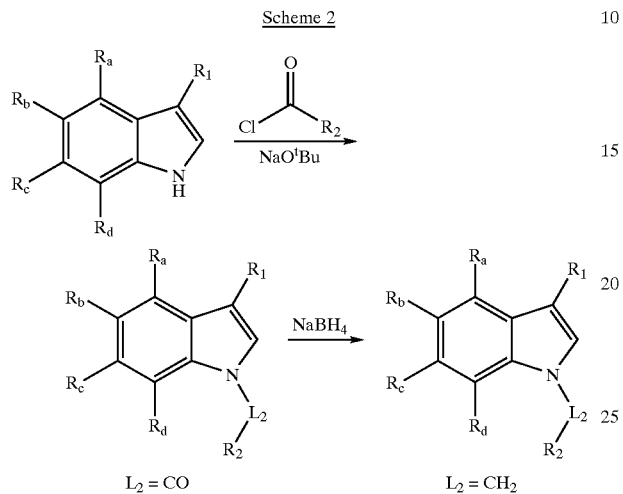

L$_2$ = CO          L$_2$ = CH$_2$

If preferred, indole compounds having other types of L$_1$ or L$_2$ can be prepared by similar coupling reactions. See the specific examples below The chemicals used in the above-described synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the indole compounds. In addition, various synthetic steps may be performed in an alternate sequence or order to give the desired compounds. Synthetic chemistry transformations and protecting group methodologies (protection and deprotection) useful in synthesizing applicable indole compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Details of synthesis of Compounds 1–54 of this invention are described in Examples 1–54, respectively.

An indole compound thus obtained can be further purified by flash column chromatography, high performance liquid chromatography, or crystallization.

Also within the scope of this invention is a pharmaceutical composition that contains an effective amount of at least one indole compound of the present invention and a pharmaceutically acceptable carrier. Further, this invention covers a method of administering to a subject in need of treating cancer an effective amount of an indole compounds described in the "Summary" section. Included in this invention are a method for inhibiting tubulin polymerization, a method for treating an angiogenesis-related disorder, and a method for inhibiting cellular proliferation or inducing the killing of hyperproliferation cells. Each of these methods includes administering to a subject in need thereof an effective amount of the aforementioned indole compounds.

As used herein, the term "treating" or "treatment" is defined as the application or administration of a composition including an indole compound to a subject, who has a disorder (e.g., cancer), a symptom of the disorder, a disease or disorder secondary to the disorder, or a predisposition toward the disorder, with the purpose to cure, alleviate, relieve, remedy, or ameliorate the disorder, the symptom of the disorder, the disease or disorder secondary to the disorder, or the predisposition toward the disorder. "An effective amount" refers to an amount of an indole compound which confers a therapeutic effect on the treated subject. The therapeutic effect may be objective (i.e., measurably by some tests or markers) or subjective (i.e., a subject gives an indication of or feels an effect). The interrelationship of dosages for animals and humans (based on milligrams per meter squared of body surface) is described in Freireich et al., (1966) *Cancer Chemother Rep* 50: 219. Body surface area may be approximately determined from height and weight of the patient. See, e.g., Scientific Tables, Geigy Pharmaceuticals, Ardley, N.Y., 1970, 537. An effective amount of the indole compounds can range from about 0.1 mg/Kg to about 1000 mg/Kg. Effective doses will also vary, as recognized by those skilled in the art, depending on the types of tumors treated, route of administration, excipient usage, and the possibility of co-usage with other therapeutic treatments such as use of other anti-cancer agents or radiation therapy. Examples of the other anti-cancer agents are paclitaxel, docitaxel, doxorubicin, daunorubicin, epirubicin, fluorouracil, melphalan, cis-platin, carboplatin, cyclophosphamide, mitomycin C, methotrexate, mitoxantrone, vinblastine, vincristine, ifosfamide, teniposide, etoposide, bleomycin, leucovorin, cytarabine, dactinomycin, interferon alpha, streptozocin, prednisolone, procarbazine, irinotecan, topotecan, colony stimulating factor, granulocyte macrophage colony stimulating factor, 1,3-bis-2-chloroethyl-1-nitroso-urea, and imatinib mesylate.

As used herein, the terms "cancer" and "hyperproliferative" refer to cells having the capacity for autonomous growth, i.e., an abnormal state or condition characterized by rapidly proliferating cell growth. Hyperproliferative disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

Examples of cellular proliferative and/or differentiative disorders include cancer, e.g., carcinoma, sarcoma, or metastatic disorders. The indole compounds described above are useful for the treatment of disease caused or exasperbated by cell proliferation. As cell proliferation inhibitors, these compounds are useful in the treatment of both primary and metastatic solid tumors and carcinomas of the breast, colon, rectum, lung, oropharynx, hypopharynx, esophagus, stomach, pancreas, liver, gallbladder, bile ducts, small intestine, urinary tract including kidney, bladder and urothelium, female genital tract including cervix, uterus, ovaries, choriocarcinoma, and gestational trophoblastic disease, male genital tract including prostate, seminal vesicles, testes, and germ cell tumors, endocrine glands including thyroid, adrenal, and pituitary, skin including hemangiomas, melanomas, sarcomas arising from bone or soft tissues including Kaposi's sarcoma, tumors of the brain, nerves, and eyes, meninges including astrocytomas, gliomas, glioblastomas, retinoblastomas, neuromas, neuroblastomas, Schwannomas and meningiomas, solid tumors arising from hematopoietic malignancies including leukemias and chloromas, plasmacytomas, plaques, tumors of mycosis fungoides, cutaneous T-cell lymphoma/ leukemia, lymphomas including Hodgkin's and non-Hodgkin's lymphomas, prophylaxis of autoimmune diseases including rheumatoid, immune and degenerative arthritis, ocular diseases including diabetic retinopathy, retinopathy of prematurity, corneal graft rejection, retrolental fibroplasia, neovascular glaucoma, rubeosis, retinal neovascularization due to macular degeneration, hypoxia, abnormal neovascularization conditions of the eye, skin diseases including psoriasis, blood vessel diseases including hemagiomas and capillary proliferation within atherosclerotic plaques, Osler-Webber Syndrome, myocardial angiogenesis, plaque neovascularization, telangiectasia, hemophiliac joints, angiofibroma, and wound granulation. In addition, cancer can be a drug resistance phenotype wherein cancer cells express P-glycoprotein, multidrug resistance-associated proteins, lung cancer resistance-associated proteins, breast cancer resistance proteins, or other proteins associated with resistance to anti-cancer drugs.

The term "angiogenesis" refers to the growth of new blood vessels—an important natural process occurring in the body. In many serious diseases states, the body loses control over angiogenesis. Angiogenesis-dependent diseases result when new blood vessels grow excessively. Examples of angiogenesis-related disorders include cardiovascular diseases (e.g., atherosclerosis), chronic inflammation (e.g., rheutatoid arthritis or Crohn's disease), diabetes (e.g., diabetic retinopathy), macular degeneration, psoriasis, endometriosis, and ocular disorders (e.g., corneal or retinal neovascularization).

To practice the method of the present invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mamlitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. An indole compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the indole compounds, or one or more solubilizing agents, can be utilized as pharmaceutical excipients for delivery of the indole compounds. Examples of other carriers include colloidal silicon dioxide, magnesium stearate, cellulose, sodium lauryl sulfate, and D&C Yellow # 10.

The indole compounds can be preliminarily screened for their efficacy in treating cancer by one or more of the following in vitro assays.

In one assay, an indole compound is tested for its cytotoxicity on MCF-7 cells (a breast carcinoma cell line). More specifically, cells are incubated with a test compound for 24 hr. The cytotoxic effect can be determined using the MTS (3-(4,5-dimethylthiazol-2-yl)-5-(3-carboxymethoxyphenyl)-2-(4-sulfophenyl)-2H-tetrazolium, inner salt) assay method described in Goodwin et al. (1995, *J. Immunol. Methods.* 179: 95–103). Cytotoxicity of the test compound is expressed in terms of $IC_{50}$ values (i.e., the concentration of the test compound which achieves a half-maximal inhibition of cell growth).

In another assay, an indole compound is tested for its cytotoxicity in cell cultures and polymerization of tubulin in the absence of GTP. The cytotoxicity is determined using the turbidimetric assay of microtubule protein described by Lopes et al. (1997 *Cancer Chemother. Pharmacol.* 41: 37–47). Tubulin polymerization is monitored spectrophotometrically by following changes in turbidity as a measure of polymer mass.

The anti-cancer activity of an indole compound can be further assessed using an in vivo animal model. See the specific example below.

Without further elaboration, it is believed that the above description has adequately enabled the present invention.

The following specific embodiments are, therefore, to be construed as merely illustrative, and not limitative of the remainder of the disclosure in any way whatsoever. All of the publications cited herein are hereby incorporated by reference in their entirety.

EXAMPLE 1

Synthesis of Compound 1: (6-methoxy-1H-indol-3-yl)-(3,4,5-trimethoxy-phenyl)-methanone

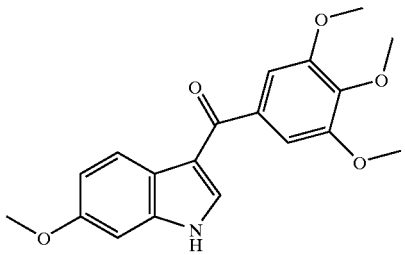

To a mixture of 6-methoxyindole (0.3 g, 2.03 mmol) and anhydrous $ZnCl_2$ (0.56 g, 4.07 mmol) in $CH_2Cl_2$ (10 mL), EtMgBr (0.9 ml, 3 M) was added over 10 min at room temperature. The obtained suspension was stirred for 1 hr. To the suspension, the solution of 3,4,5-trimethoxybenzoyl chloride/$CH_2Cl_2$ (10 ml) was added dropwisely during 5 min for a coupling reaction. The reaction mixture continued stirring for another 1 hr and $AlCl_3$ (0.27 g, 2.03 mmol) was added. The resultant thick mixture was vigorously stirred for 5 hr while monitoring by TLC (EtOAc:n-hexane=1:1). The reaction was quenched with $H_2O$ (10 ml) and extracted with $CH_2Cl_2$ (10 mL×3). The combined extracts was dried by $MgSO_4$, and evaporated to give a brown oil which was chromatographed (silica gel; EtOAc:n-hexane=1:1) to afford Compound 1 (0.5 g, 72%) as a white solid.

$^1$H NMR (CDCl$_3$), δ (ppm): 3.77 (s, 3H), 3.83 (s, 3H), 3.92 (s, 6H), 6.85 (d, J=2.1 Hz, 1H), 6.93 (dd, J=8.9, 2.4 Hz, 1H), 7.08 (s, 2H), 7.59 (s, 1H), 8.22 (d, J=8.7 Hz, 1H), 9.80 (br, 1H, NH).

MS (EI): m/z 342 (M+H).

EXAMPLE 2

Synthesis of Compound 2: (6-methyl-1H-indol-3-yl)-(3,4,5-trimethoxy-phenyl)-methanone

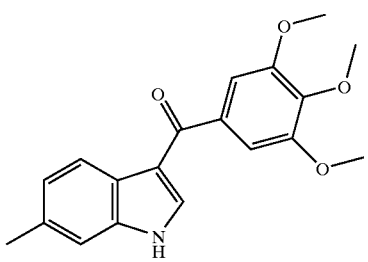

Compound 2 was prepared in a similar manner as described in Example 1.

$^1$H NMR (CDCl$_3$), δ (ppm): 2.45 (s, 3H), 3.85 (s, 6H), 3.92 (s, 6H), 7.09 (s, 2H), 7.13 (dd, J=8.4, 0.9 Hz, 1H), 7.20 (d, J=0.6 Hz, 1H), 7.63 (d, J=2.7 Hz, 1H), 8.22 (d, J=8.1 Hz, 1H), 9.36 (br, 1H, NH).

MS (EI): m/z 326 (M+H).

EXAMPLE 3

Synthesis of Compound 3: (6-methoxy-1-pyridin-4-ylmethyl-1H-indol-3-yl)-(3,4,5-trimethoxy-phenyl)-methanone

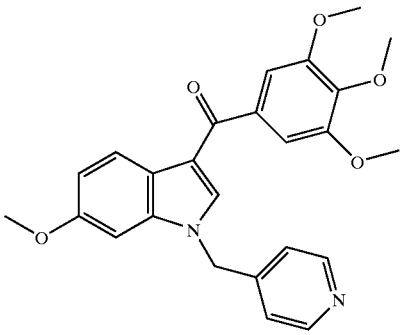

To a stirred solution of Compound 1 (0.07 g, 0.20 mmol), NaOtBu (0.08 g, 0.82 mmol), and 4-picoyl chloride hydrochloride (0.06 g, 0.41 mnol) in THF (10 mL) was heated to reflux. After 15 hr, the reaction mixture was evaporated, and the residue was extracted with $CH_2Cl_2$ (10 mL×3). The combined extracts were dried by $MgSO_4$ and evaporated to give a yellow oil which was chromatographied by silica gel (EtOAc:n-hexane=2:1) to afford Compound 3 (0.10 g, 83%) as a white solid.

$^1$H NMR (CDCl$_3$), δ (ppm): 3.80 (s, 3H), 3.86 (s, 6H), 3.90 (s, 3H), 5.42 (s, 2H), 6.64 (d, J=2.1 Hz, 1H), 7.00 (dd, J=8.7, 2.1 Hz, 1H), 7.08 (s, 2H), 7.10–7.13 (m, 2H), 7.59 (s, 1H), 8.27 (d, J=9.0 Hz, 1H).

MS (EI): m/z 433 (M+H).

EXAMPLE 4

Synthesis of Compound 4: (1-allyl-6-methoxy-1H-indol-3-yl)-(3,4,5-trimethoxy-phenyl)-methanone

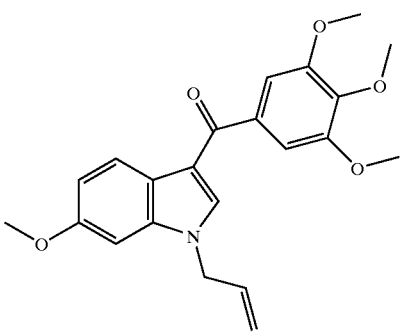

Compound 4 was prepared in a similar manner as described in Example 3.

$^1$H NMR (CDCl$_3$), δ (ppm): 3.85 (s, 3H), 3.87 (s, 6H), 3.90 (s, 3H), 4.69–4.71 (m, 2H), 5.12–5.28 (m, 2H), 5.94–6.03 (m, 1H), 6.79 (d, J=2.4 Hz, 1H), 6.95 (dd, J=8.7, 2.4 Hz, 1H), 7.07 (s, 2H), 7.51 (s, 1H), 8.23 (d, J=8.7 Hz, 1H).

MS (EI): m/z 382 (M+H).

EXAMPLE 5

Synthesis of Compound 5: [6-methoxy-1-(pyridine-2-carbonyl)-1H-indol-3-yl]-(3,4,5-trimethoxy-phenyl)-methanone

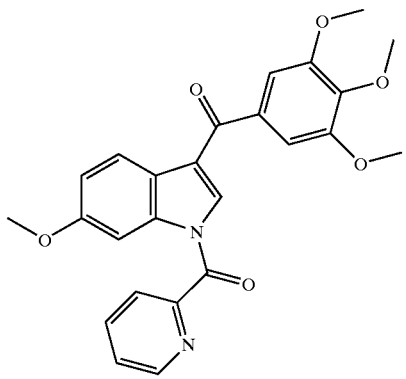

To a solution of Compound 1 (0.1 g, 0.29 mmol) in THF (15 mL) was added NaOtBu (0.11 g, 1.17 mmol) in a portion and stirred at room temperature for 15 min. The resulting dark green mixture was added picolinoyl chloride hydrochloride (0.1 g, 0.58 mmol) and then kept stirring at room temperature. After 15 hr, the reaction mixture was evaporated, and the residue was extracted with $CH_2Cl_2$ (10 mL×3). The combined extracts were dried by $MgSO_4$ and evaporated to get a yellow oil which was chromatographed by silica gel (EtOAc:n-hexane=1:1) to afford Compound 5 (0.11 g, 90%) as a white solid.

$^1$H NMR (CDCl$_3$), δ (ppm): 3.94 (s, 12H), 7.09 (dd, J=8.7, 2.4 Hz, 1H), 7.24 (s, 2H), 7.53–7.58 (m, 1H), 7.95–8.00 (m, 1H), 8.16–8.19 (m, 3H), 8.60 (s, 1H), 8.66–8.69 (m, 1H).

MS (EI): m/z 455 (M+H).

EXAMPLE 6

Synthesis of Compound 6: 6-methoxy-3-(3,4,5-trimethoxy-benzoyl)-indole-1-carboxylic acid tert-butyl ester

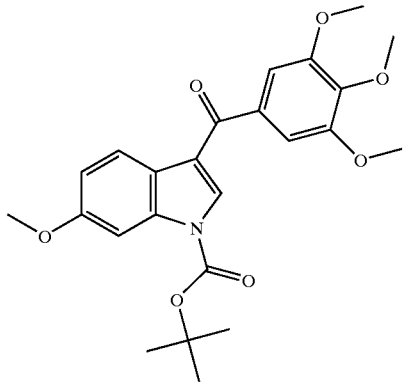

Compound 6 was prepared in a similar manner as described in Example 5.

$^1$H NMR (CDCl$_3$), δ (ppm): 1.68 (s, 9H), 3.89 (s, 3H), 3.90 (s, 6H), 3.94 (s, 3H), 7.00 (dd, J=8.9, 2.4 Hz, 1H), 7.15 (s, 2H), 7.73 (d, J=2.1 Hz, 1H), 7.99 (s, 1H), 8.13 (d, J=8.7 Hz, 1H).

MS (EI): m/z 442 (M+H).

EXAMPLE 7

Synthesis of Compound 7: (1-methanesulfonyl-6-methoxy-1H-indol-3-yl)-(3,4,5-trimethoxy-phenyl)-methanone

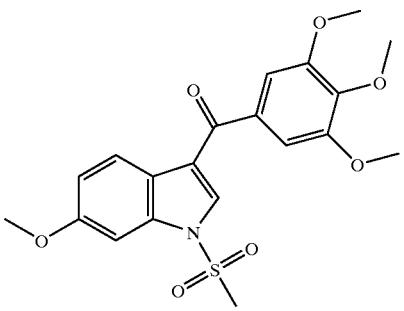

Compound 7 was prepared in a similar manner as described in Example 5.

$^1$H NMR (CDCl$_3$), δ (ppm): 3.22 (s, 3H), 3.92 (s, 9H), 3.96 (s, 3H), 7.09 (dd, J=9.0, 2.4 Hz, 1H), 7.14 (s, 2H), 7.43 (d, J=2.4 Hz, 1H), 7.84 (s, 1H), 8.20 (d, J=9.0 Hz, 1H).

MS (EI): m/z 420 (M+H).

EXAMPLE 8

Synthesis of Compound 8: [6-methoxy-1-(morpholine-4-carbonyl)-1H-indol-3-yl]-(3,4,5-trimethoxy-phenyl)-methanone

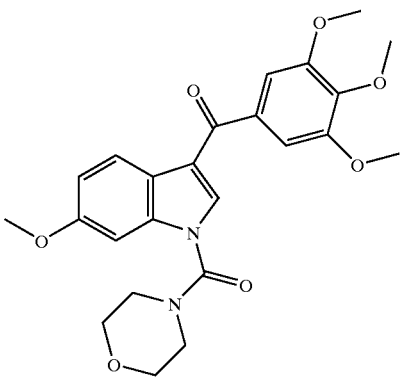

Compound 8 was prepared in a similar manner as described in Example 5.

$^1$H NMR (CDCl$_3$), δ (ppm): 3.58–3.61 (m, 4H), 3.73–3.76 (m, 4H), 3.87 (s, 9H), 3.92 (s, 3H), 6.98 (dd, J=8.9, 2.1 Hz, 1H), 7.10 (s, 2H), 7.12 (d, J=2.1 Hz, 1H), 7.68 (s, 1H), 8.13 (d, J=9.0 Hz, 1H).

MS (EI): m/z 455 (M+H).

EXAMPLE 9

Synthesis of Compound 9: [6-methoxy-1-(2-piperidin-1-yl-ethyl)-1H-indol-3-yl]-(3,4,5-trimethoxy-phenyl)-methanone

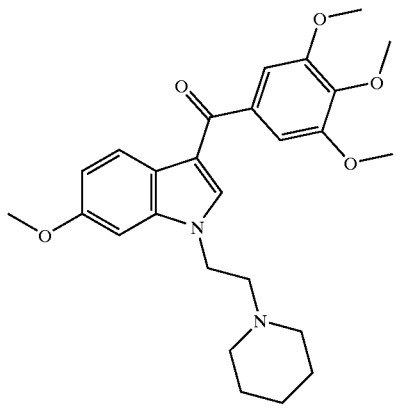

Compound 9 was prepared in a similar manner as described in Example 3.

$^1$H NMR (CDCl$_3$), δ (ppm): 1.42–1.44 (m, 2H), 1.53–1.60 (m, 4H), 2.44 (t, J=6.6 Hz, 2H), 3.88 (s, 9H), 3.91 (s, 3H), 4.22 (t, J=6.6 Hz, 2H), 6.87 (d, J=2.1 Hz, 1H), 6.96 (dd, J=8.9, 2.1 Hz, 1H), 7.08 (s, 2H), 7.60 (s, 1H), 8.23 (d, J=8.7 Hz, 1H).

MS (EI): m/z 453 (M+H).

EXAMPLE 10

Synthesis of Compound 10: (6-methoxy-1-prop-2-ynyl-1H-indol-3-yl)-(3,4,5-trimethoxy-phenyl)-methanone

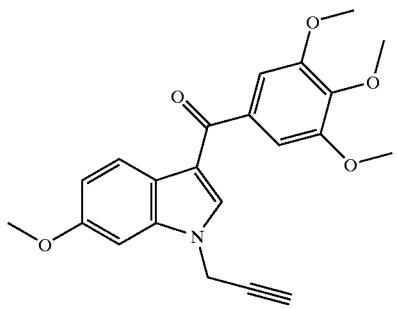

Compound 10 was prepared in a similar manner as described in Example 3.

$^1$H NMR (CDCl$_3$), δ (ppm): 3.88 (s, 9H), 3.93 (s, 3H), 5.66 (d, J=6.6 Hz, 2H), 6.95–7.16 (m, 5H), 7.58 (s, 1H), 8.20 (d, J=8.7 Hz, 1H).

MS (EI): m/z 380 (M+H).

EXAMPLE 11

Synthesis of Compound 11: 6-methoxy-3-(3,4,5-trimethoxy-benzoyl)-indole-1-carboxylic acid dimethylamide

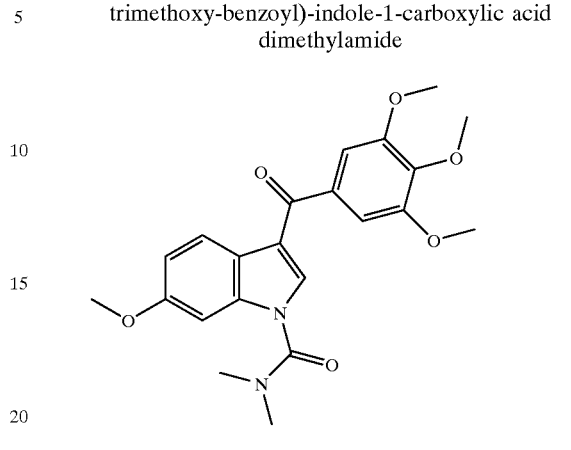

Compound 11 was prepared in a similar manner as described in Example 5.

$^1$H NMR (CDCl$_3$), δ (ppm): 3.12 (s, 6H), 3.88 (s, 3H), 3.90 (s, 6H), 3.95 (s, 3H), 7.00 (dd, J=8.7, 2.4 Hz, 1H), 7.12 (s, 2H), 7.67 (s, 1H), 8.17 (d, J=8.7 Hz, 1H).

MS (EI): m/z 413 (M+H).

EXAMPLE 12

Synthesis of Compound 12: 1-[6-methoxy-3-(3,4,5-trimethoxy-benzoyl)-indol-1-yl]-3-phenyl-propenone

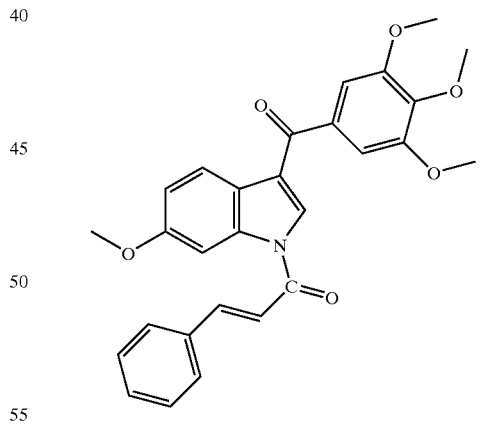

Compound 12 was prepared in a similar manner as described in Example 5.

$^1$H NMR (CDCl$_3$), δ (ppm): 3.91 (s, 6H), 3.92 (s, 3H), 3.96 (s, 3H), 7.04 (dd, J=8.7, 2.4 Hz, 1H), 7.14–7.20 (m, 3H), 7.41–7.47 (m, 3H), 7.61–7.64 (m, 2H), 8.02–8.11 (m, 4H).

MS (EI): m/z 472 (M+H).

EXAMPLE 13

Synthesis of Compound 13: 6-methoxy-3-(3,4,5-trimethoxy-benzoyl)-indole-1-carboxylic acid phenyl ester

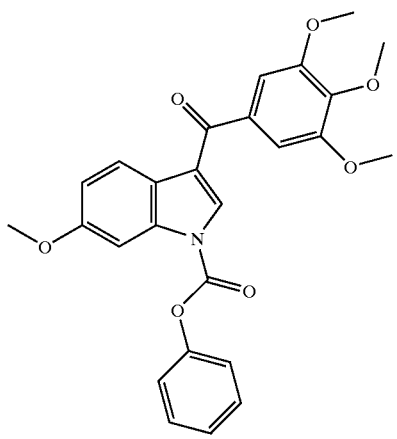

Compound 13 was prepared in a similar manner as described in Example 5.

$^1$H NMR (CDCl$_3$), δ (ppm): 3.88 (s, 3H), 3.91 (s, 6H), 3.95 (s, 3H), 7.05 (dd, J=8.9, 2.1 Hz, 1H), 7.18 (s, 2H), 7.28–7.37 (m, 3H0, 7.46–7.51 (m, 2H), 7.83 (d, J=2.1 Hz, 1H), 8.14 (s, 1H), 8.15 (d, J=9.0 Hz, 1H).

MS (EI): m/z 462 (M+H).

EXAMPLE 14

Synthesis of Compound 14: [1-(5-dimethylamino-naphthalene-1-sulfonyl)-6-methoxy-1H-indol-3-yl]-(3,4,5-trimethoxy-phenyl)-methanone

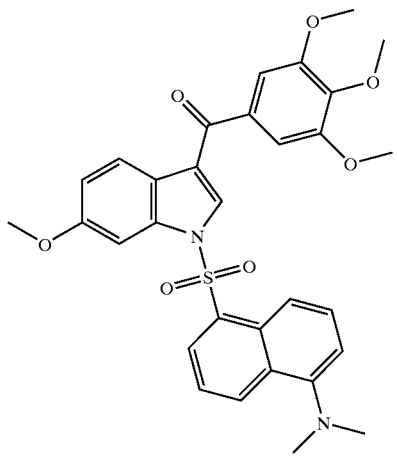

Compound 14 was prepared in a similar manner as described in Example 5.

$^1$H NMR (CDCl$_3$), δ (ppm): 2.83 (s, 6H), 3.81 (s, 3H), 3.90 (s, 6H), 3.97 (s, 3H), 6.95 (dd, J=8.9, 2.4 Hz, 1H), 7.13 (s, 2H), 7.16 (s, 1H), 7.30 (d, J=2.1 Hz, 1H), 7.48–7.55 (m, 2H), 8.10 (d, J=9.0 Hz, 1H), 8.14 (s, 1H), 8.22–8.31 (m, 2H), 8.60 (d, J=8.7 Hz, 1H).

MS (EI): m/z 575 (M+H).

EXAMPLE 15

Synthesis of Compound 15: [1-(2-dimethylamino-ethyl)-6-methoxy-1H-indol-3-yl]-(3,4,5-trimethoxy-phenyl)-methanone

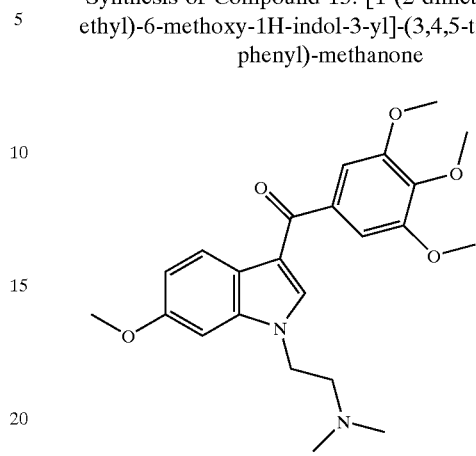

Compound 15 was prepared in a similar manner as described in Example 3.

$^1$H NMR (CDCl$_3$), δ (ppm): 2.30 (s, 6H), 2.75 (t, J=6.3 Hz, 2H), 3.89 (s, 9H), 3.92 (s, 3H), 4.22 (t, J=6.6 Hz, 2H), 6.86 (d, J=2.4 Hz, 1H), 6.97 (dd, J=8.9, 2.4 Hz, 1H), 7.10 (s, 2H), 7.62 (s, 1H), 8.25 (d, J=9.0 Hz, 1H).

MS (EI): m/z 413 (M+H).

EXAMPLE 16

Synthesis of Compound 16: (6-methoxy-1-methyl-1H-indol-3-yl)-(3,4,5-trimethoxy-phenyl)-methanone

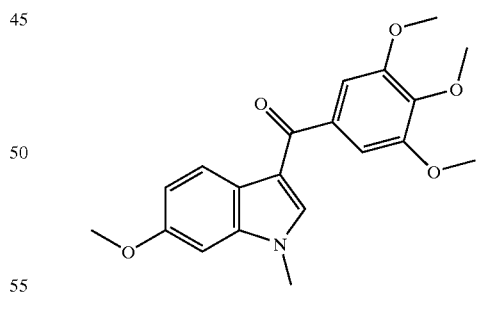

Compound 16 was prepared in a similar manner as described in Example 3.

$^1$H NMR (CDCl$_3$), δ (ppm): 3.79 (s, 3H), 3.88 (s, 9H), 3.92 (s, 3H), 6.80 (d, J=2.1 Hz, 1H), 6.95 (dd, J=9.0, 2.4 Hz, 1H), 7.07 (s, 2H), 7.47 (s, 1H), 8.23 (d, J=9.0 Hz, 1H).

MS (EI): m/z 356 (M+H).

EXAMPLE 17

Synthesis of Compound 17: [1-(2-amino-ethyl)-6-methoxy-1H-indol-3-yl]-(3,4,5-trimethoxy-phenyl)-methanone

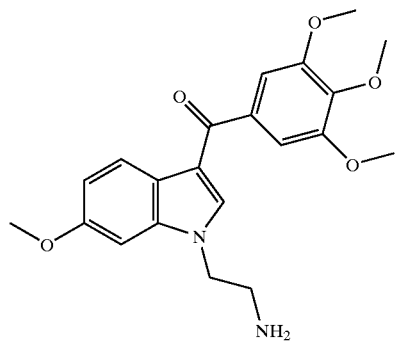

Compound 17 was prepared in a similar manner as described in Example 3.

¹H NMR (CDCl₃), δ (ppm): 1.93 (br, 2H, NH₂), 3.15 (br, 2H), 3.89 (s, 9H), 3.90 (s, 3H), 4.19 (t, J=5.1 Hz, 2H), 6.85 (d, J=2.1 Hz, 1H), 6.94 (dd, J=8.7, 2.1 Hz, 1H), 7.07 (s, 2H), 7.62 (s, 1H), 8.21 (d, J=8.4 Hz, 1H).

MS (EI): m/z 385 (M+H).

EXAMPLE 18

Synthesis of Compound 18: [1-(furan-2-carbonyl)-6-methoxy-1H-indol-3yl]-(3,4,5-trimethoxy-phenyl)-methanone

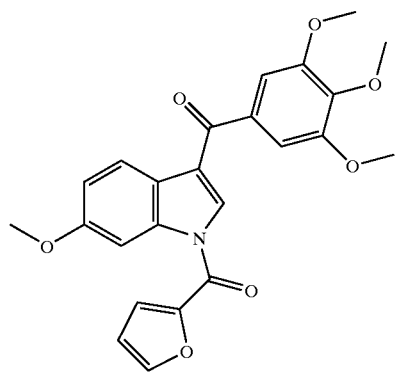

Compound 18 was prepared in a similar manner as described in Example 5.

¹H NMR (CDCl₃), δ (ppm): 3.91 (s, 9H), 3.94 (s, 3H), 6.67 (dd, J=3.6, 1.8 Hz, 1H), 7.06 (dd, J=8.7, 2.1 Hz, 1H), 7.20 (s, 2H), 7.52 (dd, J=3.6, 0.9 Hz, 1H), 7.67 (dd, J=1.8, 0.9 Hz, 1H0, 8.05 (d, J=2.4 Hz, 1H), 8.12 (d, J=8.7 Hz, 1H), 8.45 (s, 1H).

MS (EI): m/z 436 (M+H).

EXAMPLE 19

Synthesis of Compound 19: (1-ethyl-6-methoxy-1H-indol-3-yl)-(3,4,5-trimethoxy-phenyl)-methanone

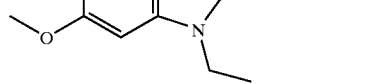

Compound 19 was prepared in a similar manner as described in Example 3.

¹H NMR (CDCl₃), δ (ppm): 1.49 (t, J=7.2 Hz, 3H), 3.88 (s, 9H), 3.91 (s, 3H), 4.15 (q, J=7.5 Hz, 2H), 6.82 (d, J=2.4 Hz, 1H), 6.95 (dd, J=9.0, 2.4 Hz, 1H), 7.07 (s, 2H), 7.54 (s, 1H), 8.22 (d, J=9.0 Hz, 1H).

MS (EI): m/z 370 (M+H).

EXAMPLE 20

Synthesis of Compound 20: [6-methoxy-1-(2-morpholin-4-yl-ethyl)-1H-indol-3-yl]-(3,4,5-trimethoxy-phenyl)-methanone

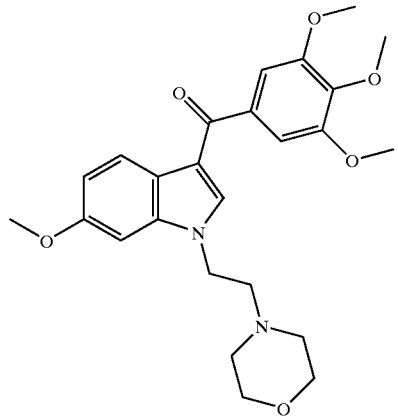

Compound 20 was prepared in a similar manner as described in Example 3.

¹H NMR (CDCl₃), δ (ppm): 2.48 (t, J=4.2 Hz, 4H), 2.79 (t, J=6.6 Hz, 2H), 3.66 (t, J=4.5 Hz, 4H), 3.87 (s, 9H), 3.91 (s, 3H), 4.22 (t, J=6.6 Hz, 2H), 6.85 (d, J=2.1 Hz, 1H), 6.95 (dd, J=8.7, 2.4 Hz, 1H), 7.07 (s, 2H), 7.58 (s, 1H), 8.21 (d, J=9.0 Hz, 1H).

MS (EI): m/z 455 (M+H).

EXAMPLE 21

Synthesis of Compound 21: [1-(4-chloro-benzyl)-6-methoxy-1H-indol-3-yl]-(3,4,5-trimethoxy-phenyl)-methanone

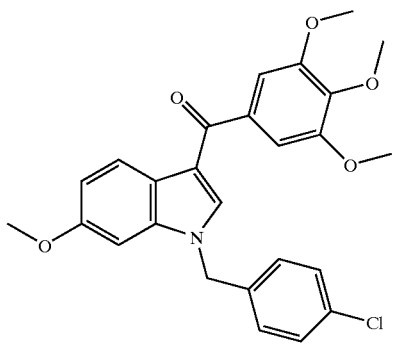

Compound 21 was prepared in a similar manner as described in Example 3.

$^1$H NMR (CDCl$_3$), δ (ppm): 3.80 (s, 3H), 3.81 (s, 6H), 3.89 (s, 3H), 5.24 (s, 2H), 6.73 (d, J=2.1 Hz, 1H), 6.95 (dd, J=8.7, 2.1 Hz, 1H), 7.03 (s, 2H), 7.06 (d, J=6.9 Hz, 2H), 7.26 (d, J=6.6 Hz, 2H), 7.49 (s, 1H), 8.24 (d, J=8.7 Hz, 1H).

MS (EI): m/z 466 (M+H).

EXAMPLE 22

Synthesis of Compound 22: (1-benzyl-6-methoxy-1H-indol-3-yl)-(3,4,5-trimethoxy-phenyl)-methanone

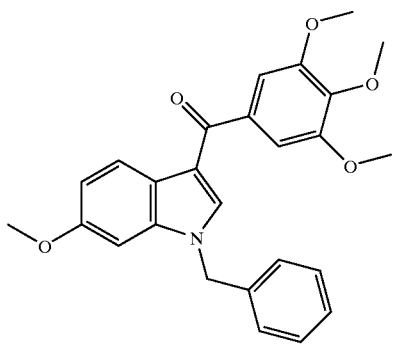

Compound 22 was prepared in a similar manner as described in Example 3.

$^1$H NMR (CDCl$_3$), δ (ppm): 3.82 (s, 9H), 3.90 (s, 3H), 5.28 (s, 2H), 6.80 (d, J=2.1 Hz, 1H), 6.98 (dd, J=8.7, 2.1 Hz, 1H), 7.05 (s, 2H), 7.18 (m, 2H), 7.32 (m, 3H), 7.50 (s, 1H), 8.27 (d, J=9.0 Hz, 1H).

MS (EI): m/z 432 (M+H).

EXAMPLE 23

Synthesis of Compound 23: (6-fluoro-1H-indol-3-yl)-(3,4,5-trimethoxy-phenyl)-methanone

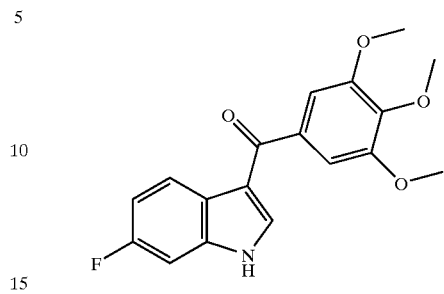

Compound 23 was prepared in a similar manner as described in Example 1.

$^1$H NMR (CDCl$_3$), δ (ppm): 3.74 (s, 3H), 3.84 (s, 6H), 7.06–7.13 (m, 3H), 7.28 (dd, J=9.6, 2.4 Hz, 1H), 8.10 (s, 1H), 8.19–8.23 (m, 1H), 12.06 (br, 1H, NH).

MS (EI): m/z 330 (M+H).

EXAMPLE 24

Synthesis of Compound 24: (6-bromo-1H-indol-3-yl)-(3,4,5-trimethoxy-phenyl)-methanone

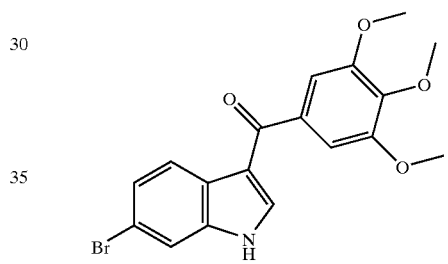

Compound 24 was prepared in a similar manner as described in Example 1.

$^1$H NMR (CDCl$_3$), δ (ppm): 3.73 (s, 3H), 3.86 (s, 6H), 7.09 (s, 2H), 7.38 (dd, J=8.4, 1.8 Hz, 1H), 7.70 (d, J=1.2 Hz, 1H), 8.14 (s, 1H), 8.17 (d, J=8.4 Hz, 1H), 12.13 (br, 1H, NH).

MS (EI): m/z 390 (M+H).

EXAMPLE 25

Synthesis of Compound 25: (4,5,6-trimethoxy-1H-indol-3-yl)-(3,4,5-trimethoxy-phenyl)-methanone

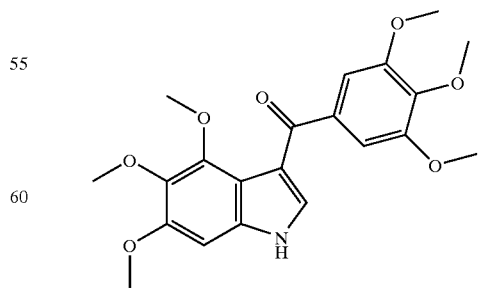

Compound 25 was prepared in a similar manner as described in Example 1.

¹H NMR (CDCl₃), δ (ppm): 3.72 (s, 3H), 3.76 (s, 6H), 3.78 (s, 6H), 3.83 (s, 3H), 6.82 (s, 1H), 7.10 (s, 2H), 7.67 (d, J=3.0 Hz, 1H), 11.69 (br, 1H, NH).

MS (EI): m/z 402 (M+H).

EXAMPLE 26

Synthesis of Compound 26: 6-methoxy-3-(3,4,5-trimethoxy-benzyl)-1H-indole

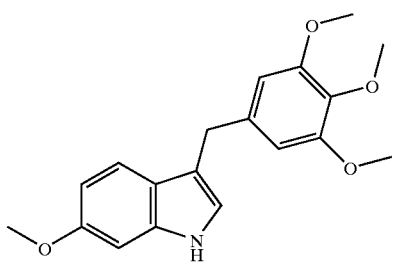

To a stirred solution of (6-Methoxy-1H-indol-3-yl)-(3,4,5-trimethoxy-phenyl)-methanone (Compound 1) (90 mg, 0.26 mmol) and NaBH₄ (98 mg, 2.6 mmol) in ethanol (10 mL) was heated to reflux. After 24 h, the reaction mixture was quenched by H₂O at 0° C. and extracted by CH₂Cl₂ (10 mL×3). The combined organic layer was dried by MgSO₄, then chromatographed under the conditions (EA:n-hexane=1:2) to afford Compound 26 as a colorless oil.

¹H NMR (CDCl₃), δ (ppm): 3.79 (s, 9), 3.83 (s 3H), 4.02 (s, 2H), 6.52 (s, 2H), 6.77 (dd, J=8.7, 2.1 Hz, 1H), 6,81 (s, 1H), 6.84 (d, J=2.1 Hz, 1H), 7.40 (d, J=8.7 Hz, 1H), 8.03 (br, 1H, NH).

MS (EI): m/z 328 (M+H).

EXAMPLE 27

Synthesis of Compound 27: (5-methoxy-indol-1-yl)-(3,4,5-trimethoxy-phenyl)-methanone

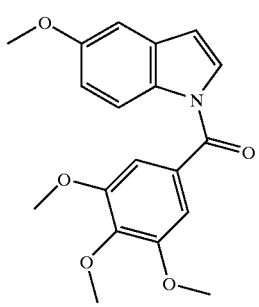

To a solution of 5-methoxyindole (1 g, 6.79 mmol) in THF (30 mL) was added NaO^tBu (0.98 g, 10.19 mmol) and stirred at room temperature for 15 min. 3,4,5-trimethoxybenzoyl chloride (2.35 g, 10.19 mmol) was added to the reaction mixture in one portion. After 15 hr, it was evaporated, and the residue was extracted with CH₂Cl₂ (20 mL×3). The combined extracts were dried by MgSO₄ and evaporated to give a yellow oil which was chromatographed by silica gel (EtOAc:n-hexane=1:3) to afford Compound 26 (2.03 g, 88%) as a pale white solid.

¹H NMR (CDCl₃), δ (ppm): 3.91 (s, 9H), 3.94 (s, 3H), 6.56 (d, J=3.6 Hz, 1H), 6.95 (s, 2H), 7.00 (m, 1H), 7.07 (d, J=2.4 Hz, 1H), 7.34 (d, J=3.6 Hz, 1H), 8.27 (d, J=9.0 Hz, 1H).

MS (EI): m/z 342 (M+H).

EXAMPLE 28

Synthesis of Compound 28: (6-fluoro-indol-1-yl)-(3,4,5-trimethoxy-phenyl)-methanone

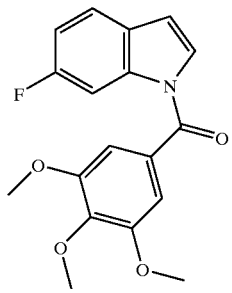

Compound 28 was prepared in a similar manner as described in Example 27.

¹H NMR (CDCl₃), δ (ppm): 3.90 (s, 6H), 3.96 (s, 3H), 6.60 (dd, J=3.6, 0.6 Hz, 1H), 6.98 (s, 2H), 7.05–7.12 (m, 1H), 7.37 (d, J=3.9 Hz, 1H), 7.51–7.55(m, 1H), 8.14 (dd, J=10.2, 2.4 Hz, 1H).

MS (EI): m/z 330 (M+H).

EXAMPLE 29

Synthesis of Compound 29: (5,6-dimethoxy-indol-1-yl)-(3,4,5-trimethoxy-phenyl)-methanone

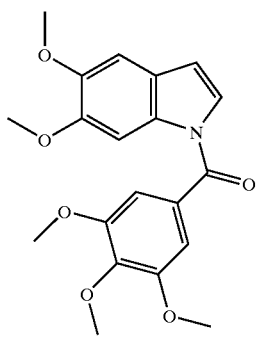

Compound 29 was prepared in a similar manner as described in Example 27.

¹H NMR (CDCl₃), δ (ppm): 3.88 (s, 6H), 3.92 (s, 3H), 3.94 (s, 3H), 3.96 (s, 3H), 6.51 (d, J=3.6 Hz, 1H), 6.96 (s, 2H), 7.07 (s, 1H), 7.22 (d, J=3.6 Hz, 1H), 8.03 (s, 1H).

MS (EI): m/z 372 (M+H).

EXAMPLE 30

Synthesis of Compound 30: (5,6-bis-benzyloxy-indol-1-yl)-(3,4,5-trimethoxy-phenyl)-methanone

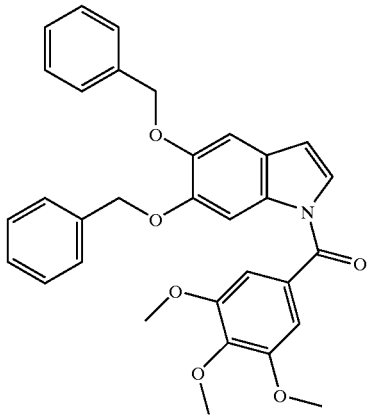

Compound 30 was prepared in a similar manner as described in Example 27.

$^1$H NMR (CDCl$_3$), δ (ppm): 3.89 (s, 6H), 3.95 (s, 3H), 5.22 (s, 2H), 5.26 (s, 2H), 6.48 (d, J=3.9 Hz, 1H), 6.96 (s, 2H), 7.12 (s, 1H), 7.22 (d, J=3.6 Hz, 1H), 7.31–7.40 (m, 6H), 7.47–7.54 (m, 4H), 8.14 (s, 1H).

MS (EI): m/z 524 (M+H).

EXAMPLE 31

Synthesis of Compound 31: [1,3]dioxolo[4,5-f]indol-5-yl-(3,4,5-trimethoxy-phenyl)-methanone

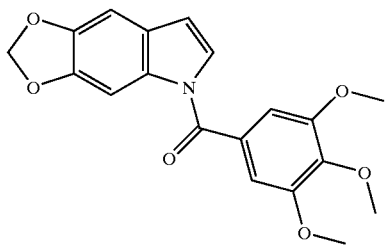

Compound 31 was prepared in a similar manner as described in Example 27.

$^1$H NMR (CDCl$_3$), δ (ppm): 3.93 (s, 6H), 3.94 (s, 3H), 6.02 (s, 2H), 6.49 (d, J=3.6 Hz, 1H), 6.97 (m, 3H), 7.23 (d, J=3.9 Hz, 1H), 7.96 (s, 1H).

MS (EI): m/z 356 (M+H).

EXAMPLE 32

Synthesis of Compound 32: [3-(2-dimethylamino-ethyl)-5-methoxy-indol-1-yl]-(3,4,5-trimethoxy-phenyl)-methanone

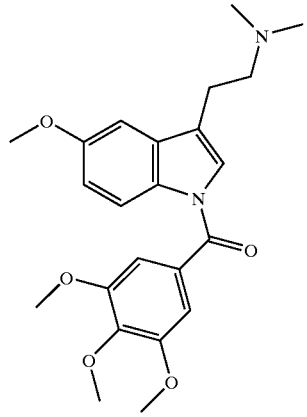

Compound 32 was prepared in a similar manner as described in Example 27.

$^1$H NMR (CDCl$_3$), δ (ppm): 2.5 (s, 6H), 2.86–2.95 (m, 4H), 3.83 (s, 9H), 3.87 (s, 3H), 6.88 (s, 2H), 6.89–6.92 (m, 1H), 7.04 (d, J=2.4 Hz, 1H), 7.14 (s, 1H), 8.14 (d, J=9.0 Hz, 1H), 9.25 (br, 1H, NH).

MS (EI): m/z 413 (M+H).

EXAMPLE 33

Synthesis of Compound 33: N-{2-[5-Methoxy-1-(3,4,5-trimethoxy-benzoyl)-1H-indol-3-yl]-ethyl}-acetamide

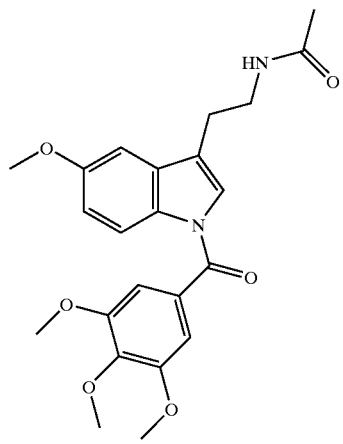

Compound 33 was prepared in a similar manner as described in Example 27.

$^1$H NMR (CDCl$_3$), δ (ppm): 1.92 (s, 3H), 2.86 (t, J=7.2Hz, 2H), 3.52 (dd, J=6.6, 13.2 Hz, 2H), 3.86 (s, 9H), 3.93 (s, 3H), 5.84 (br, 1H, NH), 6.97 (dd, J=9.0, 2.4 Hz, 1H), 7.03 (d, J=2.4 Hz, 1H), 8.18 (d, J=9.0 Hz, 1H).

MS (EI): m/z 427 (M+H).

EXAMPLE 34

Synthesis of Compound 34: (5,6-dimethoxy-1H-indol-3-yl)-(3,4,5-trimethoxy-phenyl)-methanone

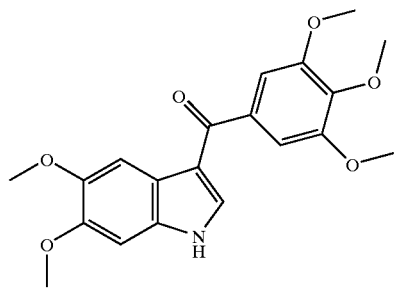

Compound 34 was prepared in a similar manner as described in Example 1.

$^1$H NMR (CDCl$_3$), δ (ppm): 3.89 (s, 6H), 3.92 (s, 6H), 3.98 (s, 3H), 6.93 (s, 1H), 7.11 (s, 2H), 7.59 (d, J=2.7 Hz, 1H), 7.91 (s, 1H), 8.72 (s, 1H).

MS(EI): m/z 372 (M+H).

EXAMPLE 35

Synthesis of Compound 35: (5-methoxy-2-methyl-indol-1-yl)-(3,4,5-trimethoxy-phenyl)-methanone

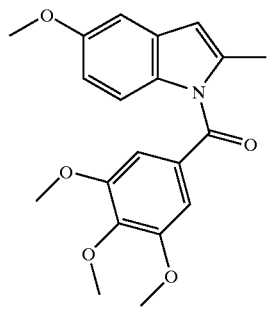

Compound 35 was prepared in a similar manner as described in Example 27.

$^1$H NMR (CDCl$_3$), δ (ppm): 2.41 (s, 3H), 3.80 (s, 9H), 3.93 (s, 3H), 6.34 (t, J=0.9 Hz, 1H), 6.65 (dd, J=9, 2.4 Hz, 1H), 6.92 (d, J=2.7 Hz, 1H), 6.95 (s, 2H), 6.97 (d, J=8.7 Hz, 1H).

MS(EI): m/z 356 (M+H).

EXAMPLE 36

Synthesis of Compound 36: (1,6-dimethyl-1H-indol-3-yl)-(3,4,5-trimethoxy-phenyl)-methanone

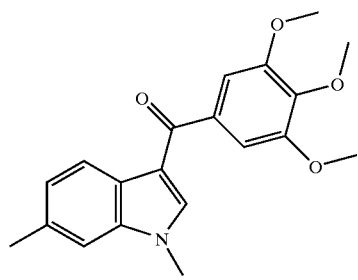

Compound 36 was prepared in a similar manner as described in Example 16.

$^1$H NMR (CDCl$_3$), δ (ppm): 2.52 (s, 3H), 3.82 (2, 3H), 3.89 (s, 6H), 3.93 (s, 3H), 7.08 (s, 2H), 7.18~7.15 (m, 2H), 7.52 (s, 1H), 8.23 (d, J=8.7 Hz, 1H).

MS(EI): m/z 340 (M+H).

EXAMPLE 37

Synthesis of Compound 37: (1-ethyl-6-methyl-1H-indol-3-yl)-(3,4,5-trimethoxy-phenyl)-methanone

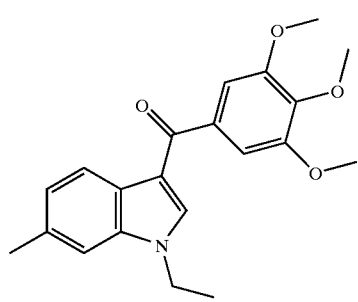

Compound 37 was prepared in a similar manner as described in Example 36.

$^1$H NMR (CDCl$_3$), δ (ppm): 1.52 (t, J=7.3 Hz, 3H), 2.53 (s, 3H), 3.90 (s, 6H), 3.93 (s, 3H), 4.20 (q, J=7.3 Hz, 2H), 7.10 (s, 1H), 7.17 (d, J=8.4 Hz, 1H), 7.20 (s, 1H), 7.60 (s, 1H), 8.23 (d, J=8.1 Hz, 1H).

MS(EI): m/z 354 (M+H).

EXAMPLE 38

Synthesis of Compound 38: (1-allyl-6-methyl-1H-indol-3-yl)-(3,4,5-trimethoxy-phenyl)-methanone

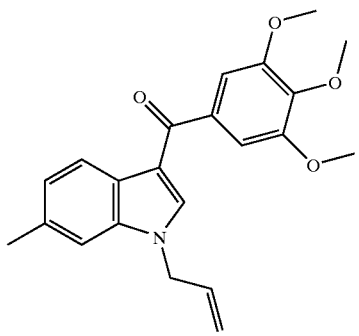

Compound 38 was prepared in a similar manner as described in Example 4.

$^1$H NMR (CDCl$_3$), δ (ppm): 2.51 (s, 3H), 3.89 (s, 6H), 3.93 (s, 3H), 4.75 (dt, J=5.4, 1.5 Hz, 2H), 5.26 (dt, J=5.4, 1.5 Hz, 2H), 5.174 (dd, J=17.1, 0.9 Hz, 1H), 5.29 (dd, J=10.5, 1.2 Hz, 1H), 7.10 (s, 2H), 7.18~7.15 (m, 2H), 7.57 (s, 1H), 8.24 (d, J=8.4 Hz, 1H).

MS(EI): m/z 366 (M+H).

EXAMPLE 39

Synthesis of Compound 39: (5-ethyl-5H-[1,3]dioxolo[4,5-f]indol-7-yl)-(3,4,5-trimethoxy-phenyl)-methanone

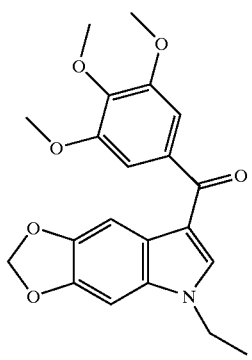

Compound 39 was prepared in a similar manner as described in Example 37.

$^1$H NMR (CDCl$_3$), δ (ppm): 1.47 (t, J=7.3 Hz, 3H), 3.90 (s, 6H), 3.93 (s, 3H), 4.132 (q, J=7.3Hz, 2H), 6.84 (s, 1H), 6.00 (s, 2H), 7.08 (s, 2H), 7.50 (s, 1H), 7.84 (s, 1H).

MS(EI): m/z 384 (M+H).

EXAMPLE 40

Synthesis of Compound 40: (5-methyl-5H-[1,3]dioxolo[4,5-f]indol-7-yl)-(3,4,5-trimethoxy-phenyl)-methanone

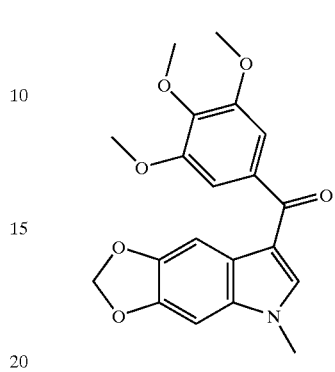

Compound 40 was prepared in a similar manner as described in Example 36.

$^1$H NMR (CDCl$_3$), δ (ppm): 3.78 (s, 3H), 3.90 (s, 6H), 3.93 (s, 3H), 6.01 (s, 2H), 6.81 (d, J=0.5 Hz, 1H), 7.07 (s, 2H), 7.43 (s, 1H), 7.83 (d, J=1 Hz, 1H).

MS(EI): m/z 370 (M+H).

EXAMPLE 41

Synthesis of Compound 41: (5-allyl-5H-[1,3]dioxolo[4,5-f]indol-7-yl)-(3,4,5-trimethoxy-phenyl)-methanone

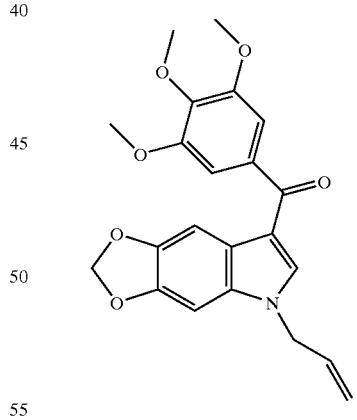

Compound 41 was prepared in a similar manner as described in Example 38.

$^1$H NMR (CDCl$_3$), δ (ppm): 3.90 (s, 6H), 3.93 (s, 3H), 4.69 (dt, J=5.4, 1.5 Hz, 2H), 5.15 (dd, J=17, 0.9 Hz, 1H), 5.29 (dd, J=9, 0.9 Hz, 1H), 6.03~5.94 (m, 3H), 7.68 (d, J=1 Hz, 1H), 7.08 (s, 2H), 7.48 (s, 1H), 7.84 (d, J=1 Hz, 1H).

MS(EI): m/z 396 (M+H).

EXAMPLE 42

Synthesis of Compound 42: (6-methoxy-2-methyl-1H-indol-3-yl)-(3,4,5-trimethoxy-phenyl)-methanone

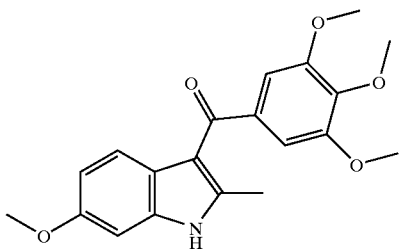

Compound 42 was prepared in a similar manner as described in Example 1.

$^1$H NMR (CDCl$_3$), δ (ppm): 2.52 (s, 3H), 3.80 (s, 9H), 3.91 (s, 3H), 6.73 (dd, J=8.7, 2.1 Hz, 1H), 6.79 (d, J=2.4 Hz, 1H), 7.05 (s, 2H), 7.35 (d, J=8.7 Hz, 1H), 8.50 (s, 1H).

MS(EI): m/z 356 (M+H).

EXAMPLE 43

Synthesis of Compound 43: 6-methoxy-3-(3,4,5-trimethoxy-phenylsulfanyl)-1H-indole

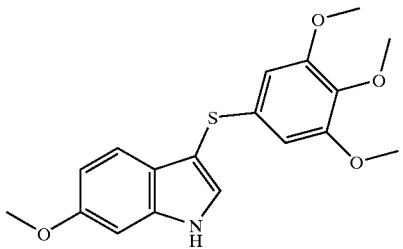

Compound 43 was prepared in a similar manner as described in Example 36.

$^1$H NMR (CDCl$_3$), δ (ppm): 3.66 (s, 3H), 3.76 (s, 6H), 3.85 (s, 3H), 6.37 (s, 2H), 6.82 (dd, J=8.4, 2.4 Hz, 1H), 6.88 (d, J=2.1 Hz, 1H), 7.37 (d, J=2.4 Hz, 1H); 7.47 (d, J=8.4 Hz, 1H), 8.29 (s, 1H).

MS(EI): m/z 346 (M+H).

EXAMPLE 44

Synthesis of Compound 44: (6-ethoxy-1H-indol-3-yl)-(3,4,5-trimethoxy-phenyl)-methanone

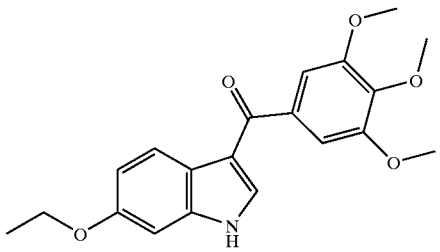

Compound 44 was prepared in a similar manner as described in Example 1.

$^1$H NMR (CDCl$_3$), δ (ppm): 1.47 (t, J=7 Hz, 3H), 3.9 (s, 6H), 3.92 (s, 3H), 4.09 (q, J=6.9 Hz, 2H), 6.92 (d, J=2.4 Hz, 1H), 6.99 (dd, J=8.7, 2.1 Hz, 1H), 7.12 (s, 2H), 7.63 (d, J=2.7 Hz, 1H), 8.63 (br, 1H, NH).

MS(EI): m/z 356 (M+H).

EXAMPLE 45

Synthesis of Compound 45: (7-methoxy-1H-indol-3-yl)-(3,4,5-trimethoxy-phenyl)-methanone

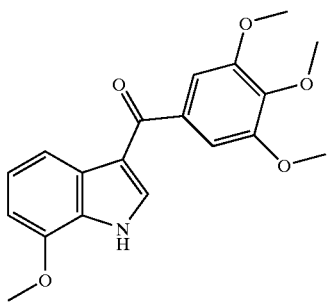

Compound 45 was prepared in a similar manner as described in Example 1.

$^1$H NMR (CDCl$_3$), δ (ppm): 3.90 (s, 6H), 3.94 (s, 3H), 3.99 (s, 3H), 6.78 (d, J=7.8 Hz, 2H), 7.13 (s, 2H), 7.26 (d, J=7.8 Hz, 1H), 7.71 (d, J=3 Hz, 1H), 7.93 (d, J=8.1, 1H), 8.96 (br, 1H, NH).

MS(EI): m/z 342 (M+H).

EXAMPLE 46

Synthesis of Compound 46: (4-Methoxy-1H-indol-3-yl)-(3,4,5-trimethoxy-phenyl)-methanone

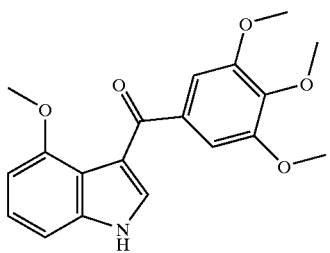

Compound 46 was prepared in a similar manner as described in Example 1.

$^1$H NMR (CDCl$_3$), δ (ppm): 3.79 (s, 6H), 3.85 (s, 3H), 3.94 (s, 3H), 6.66 (d, J=7.8 Hz, 1H), 7.08 (d, J=8.1 Hz, 1H), 7.19 (s, 2H), 7.23 (d, J=8.1 Hz, 1H), 7.54 (d, J=8.1 Hz, 1H), 8.71 (br, 1H, NH).

MS(EI): m/z 342 (M+H).

EXAMPLE 47

Synthesis of Compound 47: (5-Methoxy-4-methyl-1H-indol-3-yl)-(3,4,5-trimethoxy-phenyl)-methanone

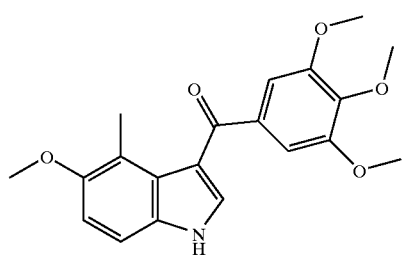

Compound 47 was prepared in a similar manner as described in Example 1.

$^1$H NMR (CDCl$_3$), δ (ppm): 2.56 (s, 3H), 3.87 (s, 6H), 3.95 (s, 3H), 6.99 (d, J=8.7 Hz, 1H), 7.19 (s, 2H), 7.22 (d, J=9.3 Hz, 1H), 7.43 (d, J=3 Hz, 1H), 9.10 (br, 1H, NH).

MS(EI): m/z 356 (M+H).

EXAMPLE 48

Synthesis of Compound 48: (4,7-dimethoxy-1H-indol-3-yl)-(3,4,5-trimethoxy-phenyl)-methanone

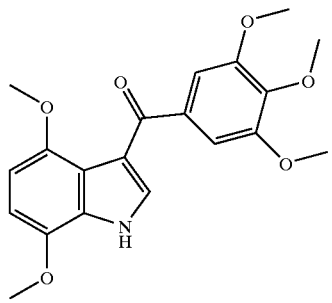

Compound 48 was prepared in a similar manner as described in Example 1.

$^1$H NMR (CDCl$_3$), δ (ppm): 3.74 (s, 3H), 3.84 (s, 6H), 3.93 (s, 3H), 3.94 (s, 3H), 6.51 (d, J=8.4, 1H), 6.64 (d, J=8.4, 1H), 7.17 (s, 2H), 7.53 (d, J=2.7 Hz, 1H), 9.00 (br, 1H, NH).

MS(EI): m/z 372 (M+H).

EXAMPLE 49

Synthesis of Compound 49: (4,6-dimethoxy-1H-indol-3-yl)-(3,4,5-trimethoxy-phenyl)-methanone

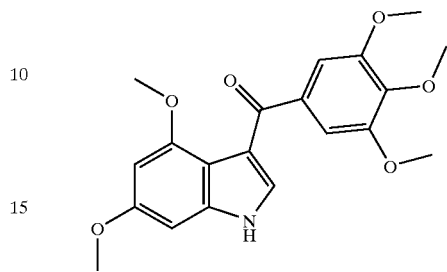

Compound 49 was prepared in a similar manner as described in Example 1.

$^1$H NMR (CDCl$_3$), δ (ppm): 3.79 (s, 3H), 3.85 (s, 3H), 3.86 (s, 6H), 3.94 (s, 3H), 6.33 (d, J=2.1 Hz, 1H), 6.55 (d, J=1.8 Hz, 1H), 7.17 (s, 2H), 7.45 (d, J=2.7 Hz, 1H), 9.17 (br, 1H, NH).

MS(EI): m/z 372 (M+H).

EXAMPLE 50

Synthesis of Compound 50: (5,7-dimethoxy-1H-indol-3-yl)-(3,4,5-trimethoxy-phenyl)-methanone

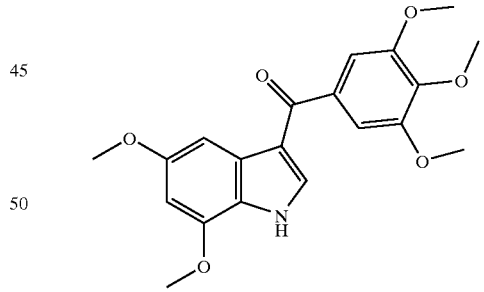

Compound 50 was prepared in a similar manner as described in Example 1.

$^1$H NMR (CDCl$_3$), δ (ppm): 3.85~3.97 (m, 15H), 6.46 (d, J=2.1 Hz, 1H), 7.48 (d, J=2.1 Hz, 1H), 7.65 (d, J=3.3 Hz, 1H), 8.79 (br, 1H, NH).

MS(EI): m/z 372 (M+H).

EXAMPLE 51

Synthesis of Compound 51: {6-methoxy-1-[4-(4-nitro-phenyl)-furan-2-ylmethyl]-1H-indol-3-yl}-(3,4,5-trimethoxy-phenyl)-methanone

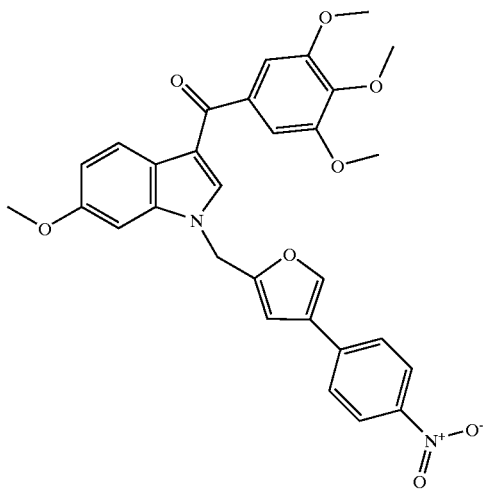

Compound 51 was prepared in a similar manner as described in Example 9.

¹H NMR (CDCl₃), δ (ppm): 3.90 (s, 6H), 3.93 (s, 3H), 5.50 (s, 2H), 6.45 (s, 1H), 6.87 (d, J=1.8 Hz, 1H), 7.01 (dd, J=8.7, 2.1 Hz, 1H), 7.11 (s, 2H), 7.66 (s, 1H), 7.89 (dd, J=6.6, 2.0 Hz, 1H), 8.27 (dd, J=6.5, 2.0 Hz, 1H), 9.08 (br, 1H, NH).

MS (EI): m/z 541 (M+H).

EXAMPLE 52

Synthesis of Compound 52: (6-hydroxy-1H-indol-3-yl)-(3,4,5-trimethoxy-phenyl)-methanone

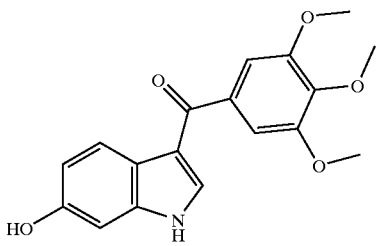

Compound 52 was prepared in a similar manner as described in Example 1.

¹H NMR (CDCl₃), δ (ppm): 3.87 (s, 3H), 3.88 (s, 6H), 6.80 (dd, J=8.4, 2.1 Hz, 1H), 6.86 (d, J=2.1 Hz, 1H), 7.08 (s, 2H), 7.65 (d, J=4.2 Hz, 1H), 8.03 (d, J=8.7 Hz, 1H), 8.95 (br, 1H).

MS (EI): m/z 328 (M+H).

EXAMPLE 53

Synthesis of Compound 53: 6-methoxy-3-(3,4,5-trimethoxy-benzenesulfonyl)-1H-indole

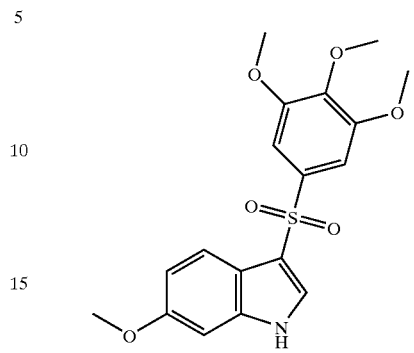

Compound 53 was prepared in a similar manner as described in Example 43.

¹H NMR (CDCl₃), δ (ppm): 3.77 (s, 3H), 3.83 (s, 3H), 3.86 (s, 6H), 6.85 (d, J=2.1 Hz, 1H), 6.89 (dd, J=8.7, 1.5 Hz, 1H), 7.25 (s, 1H), 7.72 (d, J=2.4 Hz, 1H), 7.76 (d, J=8.7 Hz, 1H), 9.11 (br, s, 1H).

MS(EI): m/z 378 (M+H).

EXAMPLE 54

Synthesis of Compound 54: [1-(2-dimethylamino-ethyl)-4,5,6-trimethoxy-1H-indol-3-yl]-(3,4,5-trimethoxy-phenyl)-methanone

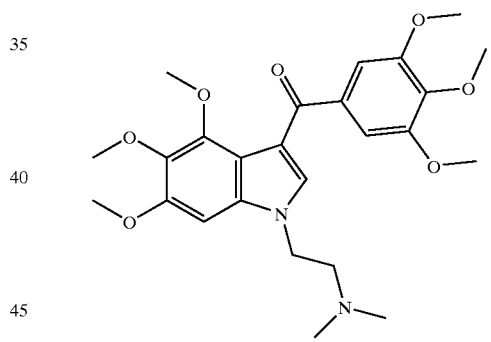

Compound 54 was prepared in a similar manner as described in Example 15.

¹H NMR (CDCl₃), δ (ppm): 2.29 (s, 6H), 2.70 (t, J=6.8 Hz, 2H), 3.87 (s, 6H), 3.89 (s, 3H), 3.92 (s, 3H), 3.94 (s, 3H), 3.94 (s, 3H), 4.15 (t, J=6.8 Hz, 2H), 6.62 (s, 1H), 7.15 (s, 1H), 7.41 (s, 3H).

MS(EI): m/z 473 (M+H).

EXAMPLE 55

In Vitro Assays

Cell Growth Inhibition Assay: MCF-7 breast carcinoma cells were maintained in plastic dishes in DMEM medium supplemented with 10% fetal bovine serum. For in vitro treatment, tumor cells were seeded in 100 mL of culture medium/well in 96-well plates to a final cell density of 6×10³ cell/mL and incubated in a CO₂ incubator at 37° C. for 24 h. The cells were treated with at least five different concentrations of a test indole compound, and incubated in a $CO_2$ incubator at 37° C. for 72 h. The number of viable cells was estimated using MTS assay and absorbance was measured at 490 nm. Cytotoxicity of the test compounds was expressed in terms of $IC_{50}$ values. The values presented represent averages of three independent experiments, each with duplicate samples.

In addition, indole compounds described in the "Summary" section were also test on HT-29 colon carcinoma cell line, as well as Hepa-G2 hepatic cell line. At least 28 compounds have $IC_{50}$ values of at least 5 $\mu$M. Unexpectedly, some of the test compounds have $IC_{50}$ values as low as <10 nM.

Tubulin Polymerization Assay: Turbidimetric assays of microtubule were performed as described by Lopes et al. (1997, *Cancer Chemother. Pharmacol.* 41: 37–47) and manual of Cytoskeleton with some modification. MAP-rich tubulin (2 mg/ml) was preincubated in polymerization buffer (0.1 M PIPES, pH 6.9, 1 mM $MgCl_2$) with drug at 4° C. for 2 min before the addition of 1 mM GTP. The samples were then rapidly warmed to 37° C. in a 96-well plate thermostatically controlled spectrophotometer and measuring the change at 350 nm with time. Results show that a test indole compound of 2 $\mu$M inhibited tubulin polymerization.

Cell Growth Inhibition Assay on Multiple-drug Resistant Human Cancer Lines: Indole compounds were tested against several panels of drug-resistant cell lines. It is well known that several anti-mitotic agents, including vinca alkaloid (vincristine, vinblastine) and taxol, have been introduced in clinic to treat various human cancers. Vinca alkaloid resistance has been attributed to a number of mechanisms associated with multi-drug resistance (MDR) phenotype including overexpression of p-glycoprotein and the multi-drug resistant-associated protein (MRP). The mechanisms responsible for taxol resistance include overexpression of p-glycoprotein and mutation of tubulin. For comparison, three anti-mitotic agents, i.e., Vincristine, VP-16, Cisplatin, CPT (camptothecin), and Taxol (paclitaxel) were also tested against several panels of drug-resistant cell lines.

KB-Vin10, a vincristine-resistant cell line derived from its parental cell line KB, showed over expression of p-glycoprotein. HONECis-6, derived from cell line HONE-1, showed resistant to an alkylating agent such as cisplatin. The mechanism of the cisplatin-resistance is under investigation. KB100, i.e., camptotnecin (CPT)-resistant cell line, displayed down regulation of topoisomerase I and an undefined mechanism responsible for drug resistance. The mechanisms responsible for VP16-resistance (KB7D) were down-regulation of topoisomerase II and overexpression of MRP 1. CPT30, a CPT-resistant cell line showed quantitatively and qualitative change of topoisomerase I. KBtaxol-5 showed mutation of tubulin.

The results shown in Table 1 indicate that indole compounds described in the "Summary" section are strong anti-mitotic agents, and are useful in treatment of various multiple-drug resistant cancers.

TABLE 1

Cytotoxicity of indole compounds against various human cancer resistant cell lines (nM)

| Cell Line<br>Cell type | KB<br>Oral | KB-Vin10<br>Vin. Res | HONE-1<br>NPC | HINECis-6<br>Cis Res. | KB100<br>CPT Res | KB100R<br>Reverse CPT Res | KB7D<br>VI-16 Res. | KB7DR<br>Reverse VP-16 Res. | KBtaxol-5<br>Taxol Res. |
|---|---|---|---|---|---|---|---|---|---|
| Compound 1 | 6 | 7 | 4 | 4.5 | 8 | 12 | 4 | 6 | 7 |
| Compound 6 | 13 | 9.6 | 19 | 19 | 18 | 18 | 8 | 15 | 37 |
| Compound 27 | 94 | 85 | 40 | 40 | 83 | 81 | 41 | 46 | 100 |
| Vincristine | 1 | 43 | 0.5 | 0.6 | | | 1920 | 337 | |
| VP-16 | 500 | | | | | | 44000 | 3500 | |
| Cisplatin | 3 | 5 | 3000 | 15000 | | | | | |
| CPT | 26 | 400 | | | 1286 | | 133 | | |
| Taxol | 10 | | | | | | | | 80 |

EXAMPLE 56

In Vivo Assay

CAM Assay for Antiangiogenic Potency: Test compounds were dissolved in a 2.5% aqueous agarose solution (final concentration: 1–20 mg/mL). For the preparation of the pellets, 10 $\mu$L of these solutions were applied dropwise on circular Teflon supports of 3 mm in diameter and then cooled to room temperature at once. After incubation at 37° C. and relative humidity of 80% for 65–70 h, the fertilized hens' eggs were positioned in a horizontal position and rotated several times. Before the opening on the snub side, 10 mL of albumin were aspirated from a hole on the pointed side. At two-third of the height (from the pointed side), the eggs were traced with a scalpel, and the shells were removed with forceps. The aperture (cavity) was covered with keep-fresh film, and the eggs were incubated at 37° C. at a relative humidity of 80% for 75 h. When the formed chorioallantoic membrane (CAM) had approximately a diameter of 2 cm, one pellet (1 pellet/egg) was placed on it. The eggs were incubated for 1 day and subsequently evaluated under the stereomicroscope. Three compounds were tested, and all show anti-angiogenesis activities.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous the indole compounds of this invention also can be made, screened for their anti-cancer activities, and used to practice this invention. Thus, other embodiments are also within the claims.

What is claimed is:

1. A compound of the following formula:

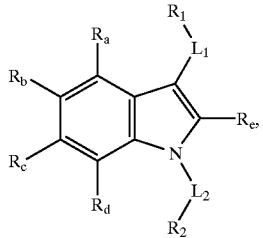

wherein
L₁ is C(O);
L₂ is a bond;
R₁ is aryl or heteroaryl, substituted with alkyloxyl;
R₂ is H, aryl, heteroaryl, halogen, nitro, nitroso, cyano, azide, isothionitro, OR, OC(O)R, OC(O)OR, OC(O)NRR', SO₂R, SO₃R, SO₂NRR', SR, NRR', NRSO₂NR'R", NRSO₂R', NRSO₃R', NRC(O)R', NRC(O)NR'R", NRC(O)OR', NRC(N)NR'R", C(O)OR, or C(O)NRR';
each of R$_a$, R$_b$, R$_c$, and R$_d$, independently, is R, halogen, nitro, nitroso, cyano, azide, isothionitro, OR, OC(O)R, OC(O)OR, OC(O)NRR', SO₂R, SO₃R, SO₂NRR', SR, NRR', NRSO₂NR'R", NRSO₂R', NRSO₃R', NRC(O)R', NRC(O)NR'R", NRC(O)OR', NRC(N)NR'R", C(O)R, C(O)OR, C(O)NRR', or R$_b$ and R$_c$, R$_a$ and R$_b$, or R$_c$ and R$_d$ taken together are O(CH₂)$_n$O; and
R$_e$ is H, alkyl, alkenyl, alkynyl, cyclyl, heterocyclyl, halogen, nitro, nitroso, cyano, azide, isothionitro, OR, OC(O)R, OC(O)OR, OC(O)NRR', SO₂R, SO₃R, SO₂NRR', SR, NRR', NRSO₂NR'R", NRSO₂R', NRSO₃R', NRC(O)R', NRC(O)NR'R", NRC(O)OR', NRC(N)NR'R", C(O)R, C(O)OR, or C(O)NRR';
in which each of R, R', and R", independently, is H, alkyl, alkenyl, alkynyl, aryl, heteroaryl, cyclyl, or heterocyclyl; and n is 1, 2, 3, 4, or 5.

2. The compound of claim 1, wherein R₁ is 5, 6, or 7-member aryl or heteroaryl tri-substituted with alkyloxy.

3. The compound of claim 2, wherein R₁ is 3,4,5-trimethoxylphenyl.

4. The compound of claim 1, wherein R$_e$ is H or alkyl.

5. The compound of claim 4, wherein R₁ is 3,4,5-trimethoxylphenyl.

6. The compound of claim 5, wherein each of R$_a$, R$_b$, R$_c$, and R$_d$, independently, is H, alkyloxy, alkyl, or halogen.

7. The compound of claim 6, wherein R$_c$ is alkyloxy, alkyl, or halogen, and each of R$_a$, R$_b$, and R$_d$ is H.

8. The compound of claim 7, wherein R₂ is H, OR, SO₂R, C(O)OR, or C(O)NRR', in which each of R and R', independently, is H, alkyl, aryl, or heteroaryl.

9. The compound of claim 5, wherein R$_b$ and R$_c$ taken together are O(CH₂)$_n$O, and each of R$_a$ and R$_d$ is H, in which n is 1 or 2.

10. The compound of claim 1, wherein the compound is
(6-Methoxy-1H-indol-3-yl)-(3,4,5-trimethoxy-phenyl)-methanone;
(6-Methyl-1H-indol-3-yl)-(3,4,5-trimethoxy-phenyl)-methanone;
6-Methoxy-3-(3,4,5-trimethoxy-benzoyl)-indole-1-carboxylic acid tert-butyl ester;
(1-Methanesulfonyl-6-methoxy-1H-indol-3-yl)-(3,4,5-trimethoxy-phenyl)-methanone;
6-Methoxy-3-(3,4,5-trimethoxy-benzoyl)-indole-1-carboxylic acid dimethylamide;
6-Methoxy-3-(3,4,5-trimethoxy-benzoyl)-indole-1-carboxylic acid phenyl ester;
[1-(5-Dimethylamino-naphthalene-1-sulfonyl)-6-methoxy-1H-indol-3-yl]-(3,4,5-trimethoxy-phenyl)-methanone;
(6-Fluoro-1H-indol-3-yl)-(3,4,5-trimethoxy-phenyl)-methanone;
(6-Bromo-1H-indol-3-yl)-(3,4,5-trimethoxy-phenyl)-methanone;
(4,5,6-Trimethoxy-1H-indol-3-yl)-(3,4,5-trimethoxy-phenyl)-methanone;
(5,6-Dimethoxy-1H-indol-3-yl)-(3,4,5-trimethoxy-phenyl)-methanone;
(6-Methoxy-2-methyl-1H-indol-3-yl)-(3,4,5-trimethoxy-phenyl)-methanone;
(6-Ethoxy-1H-indol-3-yl)-(3,4,5-trimethoxy-phenyl)-methanone;
(7-Methoxy-1H-indol-3-yl)-(3,4,5-trimethoxy-phenyl)-methanone;
(4-Methoxy-1H-indol-3-yl)-(3,4,5-trimethoxy-phenyl)-methanone;
(5-Methoxy-4-methyl-1H-indol-3-yl)-(3,4,5-trimethoxy-phenyl)-methanone;
(4,7-Dimethoxy-1H-indol-3-yl)-(3,4,5-trimethoxy-phenyl)-methanone;
(4,6-Dimethoxy-1H-indol-3-yl)-(3,4,5-trimethoxy-phenyl)-methanone;
(5,7-Dimethoxy-1H-indol-3-yl)-(3,4,5-trimethoxy-phenyl)-methanone;
(6-Hydroxy-1H-indol-3-yl)-(3,4,5- trimethoxy-phenyl)-methanone;
4-[6-Methoxy-3-(3,4,5-trimethoxy-benzoyl)-indole-1-sulfonyl]-benzoic acid; or
(5H-[1,3]Dioxolo[4,5-f]indol-7-yl)-(3,4,5-trimethoxy-phenyl)-methanone.

11. A compound of the following formula:

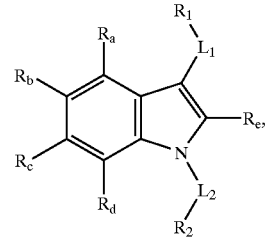

wherein
L₁ is C(O);
L₂ is a bond;
R₁ is aryl or heteroaryl;
R₂ is alkyl, alkenyl, alkynyl, cyclyl, or heterocyclyl;
each of R$_a$, R$_b$, R$_c$, and R$_d$, independently, is R, halogen, nitro, isothionitro, OR, OC(O)R, OC(O)OR, OC(O)NRR', SO₂R, SO₃R, SO₂NRR', SR, NRSO₂NR'R", NRSO₂R', NRSO₃R', NRC(O)R', NRC(O)NR'R", NRC(O)OR', NRC(N)NR'R", C(O)R, C(O)OR, C(O)NRR', or R$_b$ and R$_c$, R$_a$ and R$_b$, or R$_c$ and R$_d$ taken together are O(CH₂)$_n$O; and $R_e$ is H, alkyl, alkenyl, alkynyl, aryl, heteroaryl, cyclyl, heterocyclyl, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R'', NRC(O)OR', NRC(N)NR'R'', C(O)R, C(O)OR, or C(O)NRR';

in which each of R, R', and R'', independently, is H, alkyl, alkenyl, alkynyl, aryl, heteroaryl, cyclyl, or heterocyclyl; and n is 1, 2, 3, 4, or 5.

12. The compound of claim 11, wherein $R_1$ is 5, 6, or 7-member aryl or heteroaryl tri-substituted with alkyloxy.

13. The compound of claim 12, wherein $R_1$ is 3,4,5-trimethoxyphenyl.

14. The compound of claim 11, wherein $R_e$ is H or alkyl.

15. The compound of claim 14, wherein $R_1$ is 3,4,5-trimethoxyphenyl.

16. The compound of claim 15, wherein each of $R_a$, $R_b$, $R_c$, and $R_d$, independently, is H, alkyloxy, alkyl, or halogen.

17. The compound of claim 16, wherein $R_c$ is alkyloxy, alkyl, or halogen, and each of $R_a$, $R_b$, and $R_d$ is H.

18. The compound of claim 17, wherein $R_2$ is alkyl, alkenyl, or alkynyl.

19. The compound of claim 15, wherein $R_b$ and $R_c$ taken together are $O(CH_2)_nO$, and each of $R_a$ and $R_d$ is H, in which n is 1 or 2.

20. The compound of claim 11, wherein the compound is
(6-Methoxy-1-pyridin-4-ylmethyl-1H-indol-3-yl)-(3,4,5-trimethoxy-phenyl)-methanone;
(1-Allyl-6-methoxy-1H-indol-3-yl)-(3,4,5-trimethoxy-phenyl)-methanone;
[6-Methoxy-1-(2-piperidin-1-yl-ethyl)-1H-indol-3-yl]-(3,4,5-trimethoxy-phenyl)-methanone;
(6-Methoxy-1-prop-2-ynyl-1H-indol-3-yl)-(3,4,5-trimethoxy-phenyl)-methanone;
[1-(2-Dimethylamino-ethyl)-6-methoxy-1H-indol-3-yl]-(3,4,5-trimethoxy-phenyl)-methanone;
(6-Methoxy-1-methyl-1H-indol-3-yl)-(3,4,5-trimethoxy-phenyl)-methanone;
[1-(2-Amino-ethyl)-6-methoxy-1H-indol-3-yl]-(3,4,5-trimethoxy-phenyl)-methanone;
(1-Ethyl-6-methoxy-1H-indol-3-yl)-(3,4,5-trimethoxy-phenyl)-methanone;
[6-Methoxy-1-(2-morpholin-4-yl-ethyl)-1H-indol-3-yl]-(3,4,5-trimethoxy-phenyl)-methanone;
[1-(4-Chloro-benzyl)-6-methoxy-1H-indol-3-yl]-(3,4,5-trimethoxy-phenyl)-methanone;
(1-Benzyl-6-methoxy-1H-indol-3-yl)-(3,4,5-trimethoxy-phenyl)-methanone;
(1,6-Dimethyl-1H-indol-3-yl)-(3,4,5-trimethoxy-phenyl)-methanone;
(1-Ethyl-6-methyl-1H-indol-3-yl)-(3,4,5-trimethoxy-phenyl)-methanone;
(1-Allyl-6-methyl-1H-indol-3-yl)-(3,4,5-trimethoxy-phenyl)-methanone;
(5-Ethyl-5H-[1,3]dioxolo[4,5-f]indol-7-yl)-(3,4,5-trimethoxy-phenyl)-methanone;
(5-Methyl-5H-[1,3]dioxolo[4,5-f]indol-7-yl)-(3,4,5-trimethoxy-phenyl)-methanone;
(5-Allyl-5H-[1,3]dioxolo[4,5-f]indol-7-yl)-(3,4,5-trimethoxy-phenyl)-methanone;
{6-Methoxy-1-[4-(4-nitro-phenyl)-furan-2-ylmethyl]-1H-indol-3-yl}-(3,4,5-trimethoxy-phenyl)-methanone; or
[1-(2-Dimethylamino-ethyl)-4,5,6-trimethoxy-1H-indol-3-yl]-(3,4,5-trimethoxy-phenyl)-methanone.

21. A compound of the following formula:

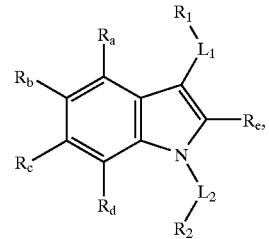

wherein $L_1$ is C(O);

$L_2$ is a bond;

$R_1$ is aryl or heteroaryl;

$R_2$ is COR''';

each of $R_a$, $R_b$, $R_c$, and $R_d$, independently, is R, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R'', NRC(O)OR', NRC(N)NR'R'', C(O)R, C(O)OR, C(O)NRR', or $R_b$ and $R_c$, $R_a$ and $R_b$, or $R_c$ and $R_d$ taken together are $O(CH_2)_nO$; and $R_e$ is R, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R'', NRC(O)OR', NRC(N)NR'R'', C(O)R, C(O)OR, or C(O)NRR';

in which each of R, R', and R'' independently, is H, alkyl, alkenyl, alkynyl, aryl, heteroaryl, cyclyl, or heterocyclyl; R''' is H, alkyl, alkenyl, alkynyl, heteroaryl, cyclyl, or heterocyclyl; and n is 1, 2, 3, 4, or 5.

22. The compound of claim 21, wherein $R_1$ is 5, 6, or 7-member aryl or heteroaryl tri-substituted with alkyloxy.

23. The compound of claim 22, wherein $R_1$ is 3,4,5-trimethoxyphenyl.

24. The compound of claim 21, wherein $R_e$ is H or alkyl.

25. The compound of claim 24, wherein $R_1$ is 3,4,5-trimethoxyphenyl.

26. The compound of claim 25, wherein each of $R_a$, $R_b$, $R_c$, and $R_d$, independently, is H, alkyloxy, alkyl, or halogen.

27. The compound of claim 26, wherein $R_c$ is alkyloxy, alkyl, or halogen, and each of $R_a$, $R_b$, and $R_d$ is H.

28. The compound of claim 27, wherein R''' is alkyl, alkenyl, heterocyclyl, or heteroaryl.

29. The compound of claim 21, wherein the compound is
[6-Methoxy-1-(pyridine-2-carbonyl)-1H-indol-3-yl]-(3,4,5-trimethoxy-phenyl)-methanone;
[6-Methoxy-1-(morpholine-4-carbonyl)-1H-indol-3-yl]-(3,4,5-trimethoxy-phenyl)-methanone;
1-[6-Methoxy-3-(3,4,5-trimethoxy-benzoyl)-indol-1-yl]-3-phenyl-propenone;
[1-(Furan-2-carbonyl)-6-methoxy-1H-indol-3-yl]-(3,4,5-trimethoxy-phenyl)-methanone;
{2-[6-Methoxy-3-(3,4,5-trimethoxy-benzoyl)-indol-1-yl]-2-oxo-ethyl}-carbamic acid 9H-fluoren-9-ylmethyl ester;
[6-Methoxy-1-(pyridine-3-carbonyl)-1H-indol-3-yl]-(3,4,5-trimethoxy-phenyl)-methanone; or
[6-Methoxy-1-(thiophene-2-carbonyl)-1H-indol-3-yl]-(3,4,5-trimethoxy-phenyl)-methanone.

30. A compound of the following formula:

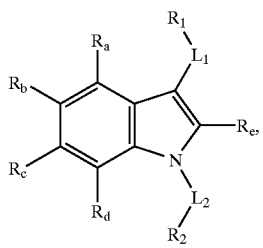

wherein $L_1$ is O, S, NR, $SO_2$, or $CH_2$;

$L_2$ is a bond;

$R_1$ is 5, 6, or 7-member aryl or heteroaryl tri-substituted with alkyloxy; and each of $R_2$, $R_a$, $R_b$, $R_c$, $R_d$, and $R_e$, independently, R, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R'', NRC(O)OR', NRC(N)NR'R'', C(O)R, C(O)OR, C(O)NRR', or $R_b$ and $R_c$, $R_a$ and $R_b$, or $R_c$ and $R_d$ taken together are $O(CH_2)_nO$;

in which each of R, R', and R'', independently, is H, alkyl, alkenyl, alkynyl, aryl, heteroaryl, cyclyl, or heterocyclyl; and n is 1, 2, 3, 4, or 5.

31. The compound of claim 30, wherein $R_1$ is 3,4,5-trimethoxylphenyl.

32. The compound of claim 30, wherein $R_e$ is H or alkyl.

33. The compound of claim 32, wherein $R_1$ is 3,4,5-trimethoxylphenyl.

34. The compound of claim 33, wherein each of $R_a$, $R_b$, $R_c$, and $R_d$, independently, is H, alkyloxy, alkyl, or halogen.

35. The compound of claim 34, wherein $R_c$ is alkyloxy, alkyl, or halogen, and each of $R_a$, $R_b$, and $R_d$ is H.

36. The compound of claim 33, wherein $R_b$ and $R_c$ taken together are $O(CH_2)_nO$, and each of $R_a$ and $R_d$ is H, in which n is 1 or 2.

37. The compound of claim 30, wherein the compound is
6-Methoxy-3-(3,4,5-trimethoxy-benzyl)-1H-indole;
6-Methoxy-3-(3,4,5-trimethoxy-phenylsulfanyl)-1H-indol; or
6-Methoxy-3-(3,4,5-trimethoxy-benzenesulfonyl)-1H-indole.

38. A compound of the following formula:

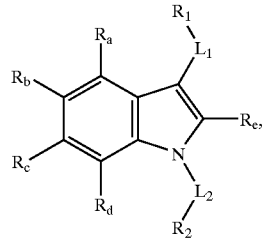

wherein $L_1$ is O, S, NR, $SO_2$, or $CH_2$;

$L_2$ is a bond;

$R_1$ is 5, 6, or 7-member aryl or heteroaryl di-substituted with alkyloxy; and each of $R_2$, $R_a$, $R_b$, $R_c$, $R_d$, and $R_e$, independently, R, halogen, nitro, nitroso, cyano, azide, isothionitro, OR, OC(O)R, OC(O)OR, OC(O)NRR', $SO_2R$, $SO_3R$, $SO_2NRR'$, SR, NRR', $NRSO_2NR'R''$, $NRSO_2R'$, $NRSO_3R'$, NRC(O)R', NRC(O)NR'R'', NRC(O)OR', NRC(N)NR'R'', C(O)R, C(O)OR, C(O)NRR', or $R_b$ and $R_c$, $R_a$ and $R_b$, or $R_c$ and $R_d$ taken together are $O(CH_2)_nO$;

in which each of R, R', and R'', independently, is H, alkyl, alkenyl, alkynyl, aryl, heteroaryl, cyclyl, or heterocyclyl; and n is 1, 2, 3, 4, or 5.

39. The compound of claim 38, wherein $R_1$ is 3,5-dimethoxylphenyl.

* * * * *